US010660972B2

(12) United States Patent
Do

(10) Patent No.: US 10,660,972 B2
(45) **Date of Patent: *May 26, 2020**

(54) METHODS FOR COUPLING TARGETING PEPTIDES ONTO RECOMBINANT LYSOSOMAL ENZYMES FOR IMPROVED TREATMENTS OF LYSOSOMAL STORAGE DISEASES

(71) Applicant: AMICUS THERAPEUTICS, INC., Cranbury, NJ (US)

(72) Inventor: Hung Do, New Hope, PA (US)

(73) Assignee: Amicus Therapeutics, Inc., Cranbury, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/347,006

(22) Filed: Nov. 9, 2016

(65) Prior Publication Data

US 2017/0319710 A1 Nov. 9, 2017

Related U.S. Application Data

(62) Division of application No. 14/122,858, filed as application No. PCT/US2012/039705 on May 25, 2012, now Pat. No. 9,545,450.

(60) Provisional application No. 61/490,957, filed on May 27, 2011.

(51) Int. Cl.

| | |
|---|---|
| ***A61K 38/16*** | (2006.01) |
| ***A61K 38/47*** | (2006.01) |
| ***C07K 14/65*** | (2006.01) |
| ***C12N 9/24*** | (2006.01) |
| ***A61K 47/68*** | (2017.01) |
| ***C12N 9/16*** | (2006.01) |
| ***A61K 47/64*** | (2017.01) |
| ***C12N 9/96*** | (2006.01) |

(52) U.S. Cl.

CPC .......... *A61K 47/6847* (2017.08); *A61K 38/47* (2013.01); *A61K 47/642* (2017.08); *C07K 14/65* (2013.01); *C12N 9/16* (2013.01); *C12N 9/2402* (2013.01); *C12N 9/96* (2013.01); *C07K 2319/00* (2013.01); *C07K 2319/21* (2013.01); *C07K 2319/50* (2013.01)

(58) Field of Classification Search

CPC .. A61K 2039/505; A61K 38/47; C07K 14/65; C07K 14/61

USPC .......... 530/303, 391.7, 397, 399; 424/178.1; 435/69.7

See application file for complete search history.

(56) References Cited

U.S. PATENT DOCUMENTS

| | | | |
|---|---|---|---|
| 7,355,018 | B2 | 4/2008 | Glass |
| 2001/0007755 | A1 | 7/2001 | Borel et al. |
| 2003/0072761 | A1 | 4/2003 | Lebowitz |
| 2006/0121018 | A1 | 6/2006 | Lebowitz |
| 2008/0241118 | A1 | 10/2008 | Lebowitz |
| 2009/0203575 | A1 | 8/2009 | LeBowitz et al. |
| 2010/0104589 | A1 | 4/2010 | Govindan et al. |

FOREIGN PATENT DOCUMENTS

| | | |
|---|---|---|
| CN | 102066422 | 5/2011 |
| WO | 2009/137721 | 11/2009 |

OTHER PUBLICATIONS

Witkowski et al. (Biochemistry 38:11643-11650, 1999.*
Rotwein et al. JBC Feb. 2, 2018, pp. 1-18.*
Korean Office Action dated Dec. 8, 2017 in Korean Patent Application No. 10-2013-7034111.
Office Action dated May 10, 2017 in Canada Patent Application No. 2,836,318.
Chinese Office Action dated Mar. 23, 2017 in Patent Application No. 201280037051.0 (with English Translation).
Japanese Decision of Rejection dated Mar. 7, 2017 in Patent Application No. 2014-513625 (with English Translation).
International Preliminary Report on Patentability and Written Opinion dated Apr. 3, 2014 in PCT/US2012/039705.
Carlos J. Fernandez, et al., "Distinct molecular events during secretory granule biogenesis revealed by sensitivities to Brefeldin A", Molecular Biology of the Cell, vol. 8, Nov. 1997, pp. 2171-2185.
English translation of the First Notification to Make Rectification dated Jul. 14, 2014 in the Chinese Patent Application No. 201280037051.0.
International Search Report dated Dec. 7, 2012 in PCT/US2012/039705.
Partial Supplementary European Search Report dated Apr. 8, 2015 in Parent Application No. 12793015.4.
Extended European Search Report dated Jul. 24, 2015 in Patent Application No. 12793015.4.
Communication Pursuant to Rules 70(2) and 70a(2) EPC dated Aug. 11, 2015 in European Patent Application No. 12793015.4.

(Continued)

*Primary Examiner* — Robert B Mondesi
*Assistant Examiner* — Mohammad Y Meah
(74) *Attorney, Agent, or Firm* — Margareta Sorenson; Hyun Joon Chung

(57) ABSTRACT

Described herein are methods of making targeting peptides conjugated to a recombinant lysosomal enzyme by modifying the amino (N)-terminus and one or more lysine residues on a recombinant human lysosomal enzyme using a first crosslinking agent to give rise to a first crosslinking agent modified recombinant human lysosomal enzyme, modifying a lysine or cysteine within a short extension linker at the carboxyl (C)-terminus on a variant IGF-2 peptide having a short extension linker using a second crosslinking agent to give rise to a second crosslinking agent modified variant IGF-2 peptide, and then conjugating the first crosslinking agent modified recombinant human lysosomal enzyme to the second crosslinking agent modified variant IGF-2 peptide containing a short extension linker. Also described herein are conjugates synthesized using the methods disclosed herein. Also described herein are treatment methods using the disclosed conjugates.

19 Claims, 7 Drawing Sheets

Specification includes a Sequence Listing.

(56) References Cited

OTHER PUBLICATIONS

Combined Chinese Office Action and Search Report dated Dec. 2, 2015 in Patent Application No. 201280037051.0 w/English translation.
Office Action dated Apr. 26, 2016 in Japanese Patent Application No. 2014-513625 w/English translation.
Office Action dated Jul. 7, 2016 in European Patent Application No. 12 793 015.4.
Devos et al., proteins: Structure, Function and Genetics, 2000, vol. 41:98-107.
Whisstock et al., Quarterly Reviews of Biophysics 2003, vol. 36 (3): 307-340.
Kisselev L., Structure, 2002, vol. 10: 8-9.
Office Action dated Feb. 19, 2019 in Japanese Patent Application No. 2017-133655 (with English language translation).
Ernst Rinderknecht, et al. "Primary Structure of Human Insulin-Like Growth Factor II", Biochemisches Institut, Universitat Zurich, CH-8028, Zurich, Switzerland, FEBS Letters, vol. 89, No. 2, pp. 283-286, May 1978.
Office Action dated Jun. 19, 2018 in Japanese Patent Application No. 2017-133655 (with English language translation).
Office Action dated May 30, 2018 in Korean Patent Application No. 10-2013-7034111 (with English language translation).

* cited by examiner

FIG. 1A

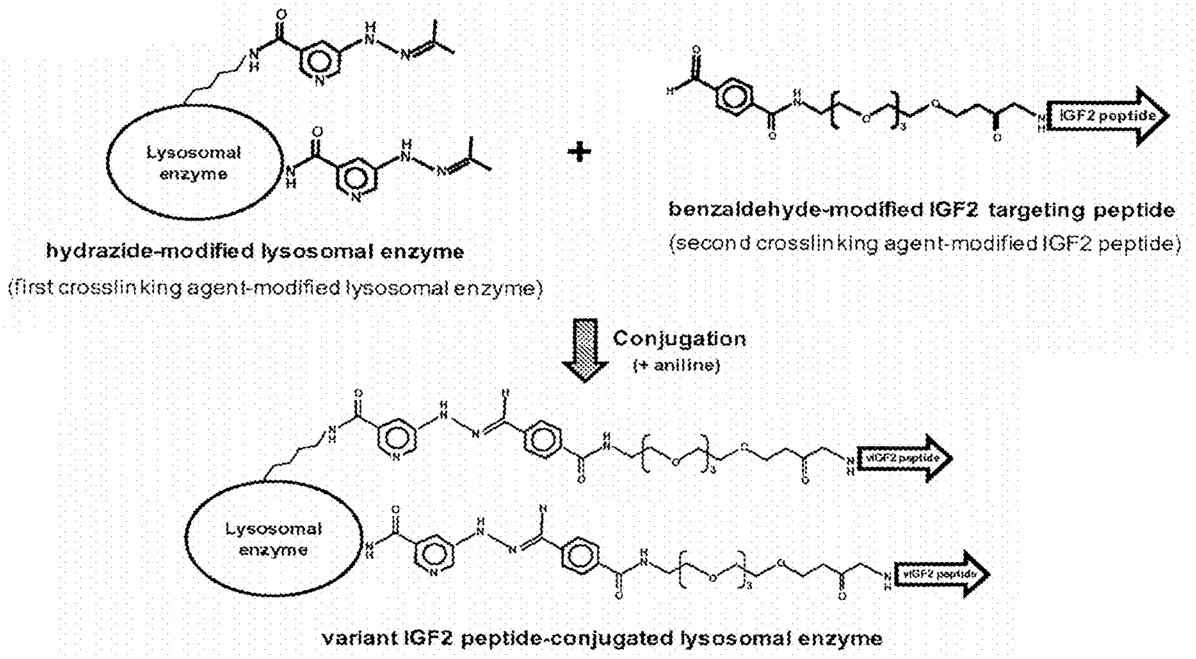

FIG. 1B

Suitable first crosslinking agents:

succinimidyl 6-hydrazinonicotinate acetone (S-Hynic)
succinimidyl 4-hydrazidoterephthalate hydrochloride (SHTH)
succinimidyl 4-hydrazinium nicotinate hydrochloride (SHNH)
*N*-hydroxysuccinimide ester-(PEG)n-hydrazide; wherein n= 3-24 PEG units

Suitable second crosslinking agents:

PEG4-pentafluorobenzyne benzoate (PEG4-PFB)
succinimidyl 4-formylbenzoate (SFB)
C6- succinimidyl 4-formylbenzoate (C6-SFB)

FIG. 2A

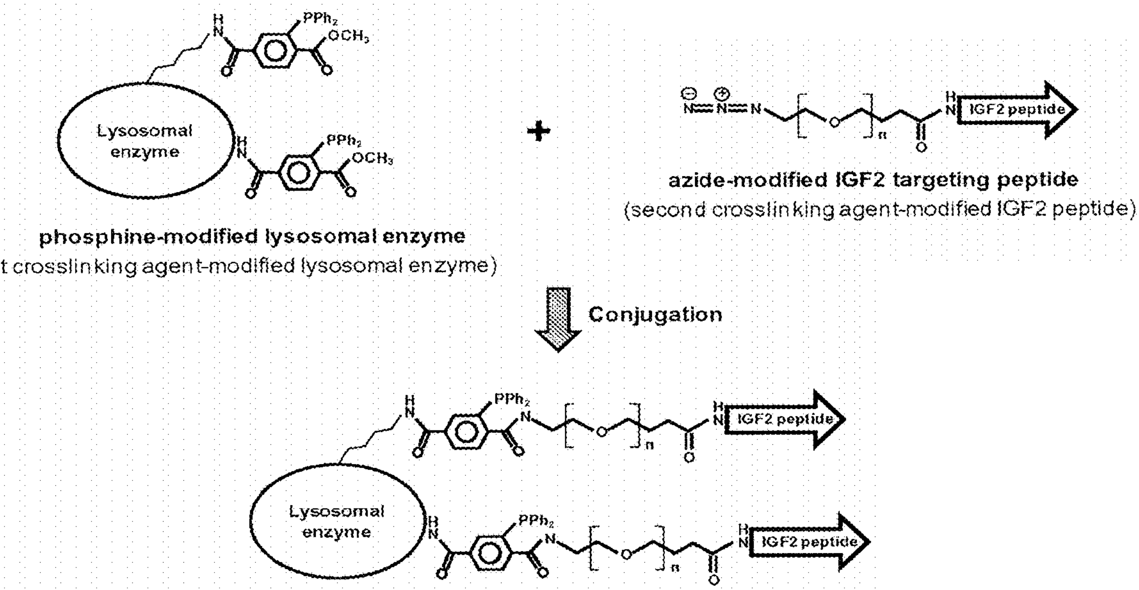

phosphine-modified lysosomal enzyme
(first crosslinking agent-modified lysosomal enzyme)

azide-modified IGF2 targeting peptide
(second crosslinking agent-modified IGF2 peptide)

variant IGF2 peptide-conjugated lysosomal enzyme

FIG. 2B

<u>Suitable first crosslinking agents:</u>

*N*-hydroxysuccinimide ester-phosphine (NHS-phosphine)
Sulfo- *N*-hydroxysuccinimide ester-phosphine (Sulfo-NHS-phosphine)

<u>Suitable second crosslinking agents:</u>

*N*-hydroxysuccinimide ester-azide (NHS-azide)
*N*-hydroxysuccinimide ester-(PEG)n-azide; wherein n=3-24 PEG units
NHS-PEG3-S-S-azide

FIG. 3A

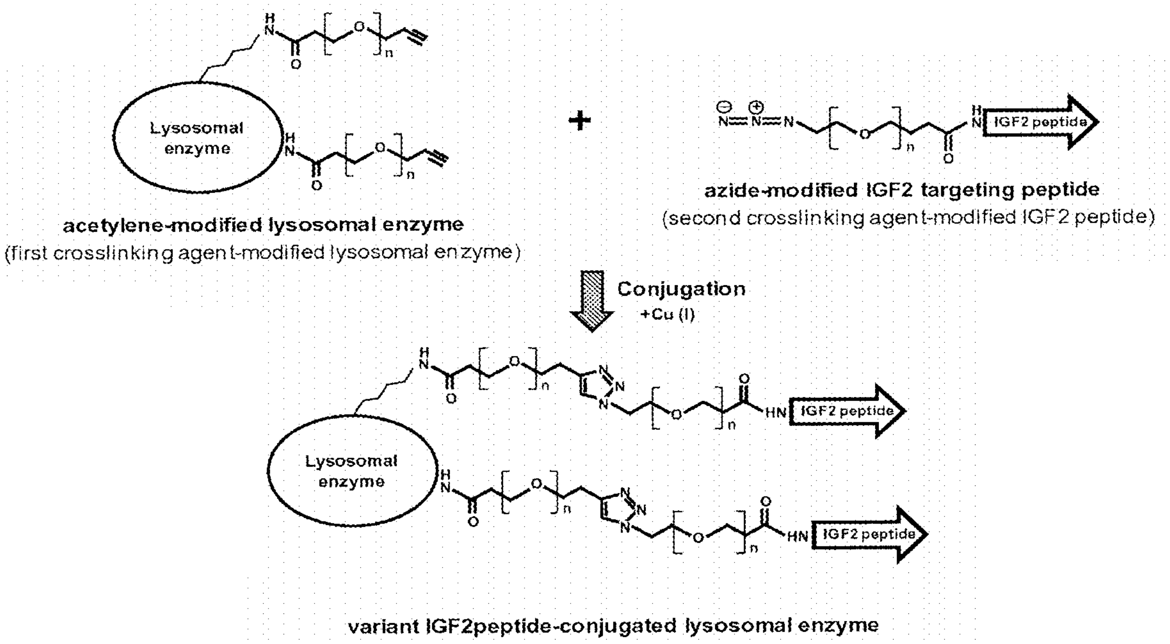

FIG. 3B

Suitable first crosslinking agents:

*N*-hydroxysuccinimide ester-tetraoxapentadecane acetylene (NHS-PEG4-acetylene)
*N*-hydroxysuccinimide ester-(PEG)n-acetylene; wherein n=3-24 PEG units
NHS-PEG3-S-S-acetylene

Suitable second crosslinking agents:

*N*-hydroxysuccinimide ester-azide (NHS-azide)
*N*-hydroxysuccinimide ester-(PEG)n-azide; wherein n=3-24 PEG units
NHS-PEG3-S-S-azide

Suitable crosslinking agents:

*m*-Maleimidobenzyol-*N*-hydroxysuccinimide ester (MBS)

Sulfo-*m*-maleimidobenzyol-*N*-hydroxysuccinimide ester (sulfo-MBS)

Sulfosuccinimidyl-4-(*N*-maleimidomethyl)cyclohexane-1-carboxylate (SMCC)

A214nm
30
20
10
0
40
4
6
8
10
Time (min)

METHODS FOR COUPLING TARGETING PEPTIDES ONTO RECOMBINANT LYSOSOMAL ENZYMES FOR IMPROVED TREATMENTS OF LYSOSOMAL STORAGE DISEASES

CROSS-REFERENCE TO RELATED APPLICATIONS

This application is a divisional of U.S. application Ser. No. 14/122,858 filed Jun. 2, 2014, which is the National Stage of International Application No. PCT/US2012/039705 filed May 25, 2012, which claims the benefit of U.S. Provisional Application No. 61/490,957, filed May 27, 2011, both of which are incorporated by reference herein in its entirety.

TECHNICAL FIELD

The technical field relates to peptide chemistry. The technical field also relates to targeting of recombinant lysosomal enzymes to the lysosome in the treatment of lysosomal storage diseases.

BACKGROUND

Lysosomes are specialized intracellular organelles where proteins, various lipids (including glycolipids and cholesterol) and carbohydrates are degraded and recycled to their primary constituents that enable synthesis of new proteins, membrane components and other molecules. Lysosomes are also utilized by cells to help maintain homeostasis and cellular health through an adaptive cellular process known as autophagy that increases lysosomal activity to provide additional amino acids for increased biosynthesis of various proteins (e.g., antibodies and interferons) and to supply nutrients for energy production to deal with stressful periods of nutrient deprivation or viral infections. Each metabolic process is catalyzed by a specific resident lysosomal enzyme. Genetic mutations can cause deficiencies in lysosomal biological activities that alter metabolic processes and lead to clinical diseases. Lysosomal storage disorders (LSDs) are a class of approximately 50 different human metabolic diseases caused by a deficiency for specific lysosomal proteins that results in the accumulation of various substances within the endosomal/lysosomal compartments. Many of these diseases have been well-characterized to understand the deficient lysosomal protein and the resultant metabolic defect. For example, there are several LSDs of altered glycolipid catabolism such as Gaucher, Fabry, and Tay-Sachs/Sandhoff. Neimann-Pick C is characterized by impaired lipid and cholesterol metabolism while diseases of altered carbohydrate metabolism such as glycogen storage diseases type II (Pompe) and type III (Corey-Forbes) have also been characterized. Other LSDs alter metabolism of bone or extracellular matrices [e.g., mucopolysaccharidoses (MPS I-VII), Gaucher] and protein turnover (neuronal ceroid lipofuscinoses; Batten, etc.). While LSDs are relatively rare, they can cause severe chronic illness and often death if not effectively treated.

There are no known cures for lysosomal storage diseases but a number of different treatment approaches have been investigated for various LSDs including bone marrow and umbilical cord blood transplantation, enzyme replacement therapy (ERT), substrate reduction therapy (SRT) and pharmacological chaperone therapy. Gene therapy is also being developed but has not been tested clinically. Of these treatment approaches, ERT is the most established with multiple ERTs approved for the treatment of various LSDs including Gaucher, Fabry, Pompe, MPS I, MPS II and MPS VI while one SRT drug is approved for the treatment of Gaucher disease.

The concept of ERT for the treatment of a lysosomal storage disease is fairly straightforward where a recombinant human lysosomal enzyme is administered in patients to supplement the deficient biological activity and improve clinical symptoms. However, unlike other protein therapeutic treatments that function primarily at the cell surface or outside of cells (e.g., anti-VEGF and other antibodies, erythropoietin, clotting factors, etc.), lysosomal enzymes must function inside cells, within lysosomes, and therefore require a mechanism for entering cells from the outside and subsequent delivery to these internal compartments. In mammals, the branched carbohydrate structures on the protein backbone on certain asparagine residues (N-linked oligosaccharides; N-glycans) for most soluble lysosomal enzymes are post-translationally modified to form a specialized carbohydrate structure called mannose 6-phosphate (M6P). M6P is the natural biological signal for identification and transport of newly synthesized lysosomal proteins from the Golgi apparatus to lysosomes via membrane-bound M6P receptors. A class of M6P receptors (cation-independent M6P receptor; CI-MPR) also cycles to the plasma membrane and is functionally active for binding and internalizing exogenous lysosomal proteins. The CI-MPR is believed to have evolved to recapture lysosomal proteins that escaped cells (via secretion out of cells) and thus, provide a targeting mechanism for internalizing exogenous lysosomal proteins and is the basis for enzyme replacement therapy for various LSDs.

Recombinant lysosomal enzyme replacement therapies have been shown to be generally safe but their effectiveness for reducing clinical symptoms varies widely. For example: Fabrazyme™ (recombinant acid α-galactosidase A; Genzyme Corp.) ERT dosed at 1 mg/kg body weight every other week is sufficient to clear accumulated substrate from endothelial cells in Fabry disease while 40 mg/kg of Myozyme™ (recombinant human acid α-glucosidase, rhGAA; Genzyme Corp.) dosed every other week is only moderately effective for Pompe disease. The disparate efficacy is primarily attributed to differences in the M6P content such that low levels of M6P correlates with poor drug targeting and lower efficacy. The manufacture of recombinant lysosomal enzymes is very challenging because it is extremely difficult to control carbohydrate processing, particularly the level of M6P in mammalian expression systems. Two specialized Golgi enzymes catalyze the M6P modification; N-acetylglucosamine phosphotransferase adds phosphate-linked N-acetylglucosamine onto certain terminal mannose residues while N-Acetylglucosamine-1-phosphodiester α-N-acetylglucosaminidase (also known as Uncovering Enzyme) removes the covering N-acetylglucosamine to reveal the M6P signal. However, N-acetylglucosamine phosphotransferase is limiting in cells and this biochemical reaction is inherently inefficient for various lysosomal proteins. Overexpression of lysosomal proteins during the manufacturing process greatly exacerbates this problem and leads to highly variable amounts of M6P. Consequently, carbohydrate processing is typically incomplete and leads to the production of recombinant lysosomal enzymes with mixtures of N-glycans that contain M6P, non-M6P structures of high-mannose type N-glycans and complex-type N-glycans (typical for secretory proteins). To complicate matters, dead or damaged cells release enzymes such as phosphatases into the cell culture medium which remove M6P. Consequently, reduced M6P content lowers the binding affinity of a recombinant lysosomal enzyme for M6P receptors and decreases its cellular uptake and thereby, reduce drug efficacy. Dead or damaged cells release other glycosidases that remove other carbohydrates (e.g., sialic acids, galactose, etc.) to reveal internal carbohydrates that are not typically exposed and these N-glycans are readily identified as aberrant. These incomplete N-glycan structures increase the clearance rate of recombinant lysosomal proteins from the circulation which can also reduce drug efficacy. Higher drug doses are therefore necessary to compensate for reduced efficacy. Higher drug dose requirements however have multiple negative implications: (1) higher drug dose could be cost-prohibitive by increasing an already expensive treatment; (2) high drug doses require long infusion times; (3) large amounts of circulating drug results in significant antibody responses (seen in most Pompe patients) and numerous patients have also experienced allergic reactions during infusions. The FDA has issued a "black-label warning" for Myozyme and the drug is typically administered very slowly at the beginning but ramped up over the course of the infusion. This strategy helps to mitigate the allergic responses but significantly lengthens infusion times where 12-hr infusions are not uncommon.

One potential strategy for improving drug targeting for various lysosomal ERTs employs a targeting peptide to efficiently target ERTs to lysosomes without requiring the traditional M6P carbohydrate structures. This is conceptually feasible since the cation-independent M6P receptor contains a distinct binding domain for a small peptide called insulin-like growth factor 2 (IGF-2) and this receptor is therefore known as the IGF-2/(IGF-2/CI-MPR). This receptor is in fact solely responsible for internalizing exogenous M6P-bearing lysosomal proteins because the IGF-2/CI-MPR is present and biologically active on the cell surface. The other class of M6P receptors, the cation-dependent M6P receptor (CD-MPR), is only involved in the transport of lysosomal proteins within cells because it is not biologically active on cell surfaces and lacks the IGF-2 peptide binding domain. The IGF-2/CI-MPR has two separate binding sites for M6P (domains 1-3 and 7-9, respectively) such that it binds a mono-M6P N-glycan (1 M6P residue on N-glycan) with moderate affinity or a bis-M6P N-glycan (two M6P residues on the same N-glycan) with approximately 3000-fold higher affinity. Since lysosomal proteins contain mixtures of complex (no M6P), mono- and bis-M6P N-glycans, their affinities for the IGF-2/CI-MPR vary widely depending on the type and amount of M6P-bearing N-glycans. The IGF-2 peptide has the highest affinity for the IGF-2/CI-MPR that is approximately 230,000-fold higher than the mono-M6P N-glycan. A summary of the binding affinities of various ligands for the IGF-2/CI-MPR are summarized below in Table 1.

TABLE 1

Ligand Affinity for IGF-2/CI-MPR

| Ligand | Binding Affinity (Apparent Kd; nM) |
| --- | --- |
| free M6P [a] | 7000 |
| pentamannose-M6P [a] | 6000 |
| bis-M6P N-Glycan [a] | 2 |
| beta-galactosidase [a] | 20 |
| WT hIGF-2 [b, c] | 0.03-0.2 |
| [Leu27] hIGF-2 [c] | 0.05 |
| [Leu27] hIGF-2 [c] | 0.06 |

In mammals, IGF-2 is the primary growth hormone during embryonic development. After birth, IGF-2 levels remain relatively constant even though it no longer mediates growth (growth mediated by IGF-1 via stimulation by human growth hormone throughout life). The role of IGF-2 after birth is not well understood but this peptide is believed to aid wound healing and tissue repair. IGF-2 is mostly bound in the circulation by serum IGF binding proteins (IGFBPs 1-6) which mediate the levels of free IGF-2 peptide. These IGFBPs also bind insulin and IGF-1 and regulate their circulating levels. The IGF-2/CI-MPR is the natural clearance pathway for free IGF-2 peptide. Because IGF-2 is structurally similar to insulin and IGF-1, it has low affinity for the insulin receptor (~100-fold lower) and IGF-1 receptor (~230-fold lower) compared to the IGF-2/CI-MPR. This specificity can be improved considerably by eliminating various amino acids or substituting specific amino acid residues (e.g., [Leu27] IGF-2 & [Leu43] IGF-2) to maintain high-affinity binding to the IGF-2/CI-MPR (Table 1) but significantly decrease or eliminate binding to the insulin and IGF-1 receptors. Similarly, IGF2 variants lacking the initial six amino acid residues or a substitution of arginine for glutamic acid at position 6 has been shown to significantly reduce affinity of IGF2 peptide for IGFBPs. Importantly, IGF-2 peptide has been shown to be safe in clinical trials and is utilized clinically to help treat certain growth deficiencies. These collective data suggest that the IGF-2 peptide potentially could be utilized as a targeting motif instead of the traditional M6P carbohydrate structures to facilitate the cellular uptake and transport of recombinant lysosomal enzymes to lysosomes.

There remains a need to develop strategies to create IGF-2-linked proteins for improved protein targeting while overcoming carbohydrate processing issues.

SUMMARY

Provided herein are methods of making a targeting peptide conjugated to a recombinant lysosomal enzyme comprising modifying the amino (N)-terminus and one or more lysine residues on a recombinant human lysosomal enzyme using a first crosslinking agent to give rise to a first crosslinking agent modified recombinant human lysosomal enzyme, modifying the first amino acid of a short extension linker at the amino (N)-terminus on a variant IGF-2 peptide using a second crosslinking agent to give rise to a second crosslinking agent modified variant IGF-2 peptide, and then conjugating the first crosslinking agent modified recombinant human lysosomal enzyme to the second crosslinking agent modified variant IGF-2 peptide containing a short extension linker.

Also provided herein are methods of making a targeting peptide conjugated to a recombinant lysosomal enzyme comprising conjugating a first crosslinking agent modified recombinant human lysosomal enzyme to one or more second crosslinking agent modified variant IGF-2 peptides where the first crosslinking agent modified recombinant lysosomal enzyme comprises a recombinant lysosomal enzyme characterized as having a chemically modified N-terminus and one or more modified lysine residues and the one or more second crosslinking agent modified variant IGF-2 peptides comprise one or more variant IGF-2 peptides comprising a modified amino acid in a short linker at the amino (N)-terminus.

Provided herein are methods of making a molecule for enzyme replacement therapy comprising conjugating a heterobifunctional crosslinking agent to a variant IGF-2 peptide and then conjugating the heterobifunctional crosslinking agent modified variant IGF-2 peptide to a recombinant human lysosomal enzyme.

Also provided herein are methods of making a molecule for enzyme replacement therapy comprising conjugating a heterobifunctional crosslinking agent to a recombinant human lysosomal enzyme and then conjugating the heterobifunctional crosslinking agent modified recombinant human lysosomal enzyme to a variant IGF-2 peptide.

Provided herein are also conjugates comprising one or more variant IGF-2 peptides chemically conjugated to a recombinant human lysosomal enzyme.

Conjugates comprising a heterobifunctional crosslinking agent modified variant IGF-2 peptide conjugated to a recombinant human lysosomal enzyme are also provided.

Provided herein are methods for treating a subject suffering from a lysosomal storage disease comprising administering to the subject a conjugate comprising one or more variant IGF-2 peptides chemically conjugated to a modified recombinant human lysosomal enzyme.

Also provided herein are methods for treating a subject suffering from a lysosomal storage disease comprising administering to the subject a conjugate comprising a heterobifunctional crosslinking agent modified variant IGF-2 peptide conjugated to a recombinant human lysosomal enzyme.

Also provided herein are methods of treating a patient suffering from Pompe, Fabry, Gaucher, MPS I, MPS II, MPS VII, Tay Sachs, Sandhoff, α-mannosidosis, or Wohlman disease comprising administering to a patient in need thereof, a composition comprising one or more variant IGF-2 peptides chemically conjugated to a recombinant lysosomal enzyme and a pharmaceutically acceptable carrier, in an amount sufficient to treat said disease.

Suitable methods of treating a patient suffering from Pompe, Fabry, Gaucher, MPS I, MPS II, MPS VII, Tay Sachs, Sandhoff, α-mannosidosis, Wohlman disease are also provided comprising administering to a patient in need thereof, a composition comprising a heterobifunctional crosslinking agent modified variant IGF-2 peptide conjugated to a recombinant human lysosomal enzyme and a pharmaceutically acceptable carrier, in an amount sufficient to treat said disease.

Provided herein is DNA sequence that encodes a variant IGF-2 peptide that was optimized for expression in *E. coli* comprising SEQ ID NO: 1.

Also provided herein are amino acids sequence that represents a variant IGF-2 peptide comprising SEQ ID NO: 2.

Amino acid sequences that represents an extension linker comprising SEQ ID NO: 3 are also provided.

BRIEF DESCRIPTION OF THE DRAWINGS

The foregoing and other aspects of the present invention is apparent from the following detailed description of the invention when considered in conjunction with the accompanying drawings. For the purpose of illustrating the invention, there is shown in the drawings embodiments that are presently preferred, it being understood, however, that the invention is not limited to the specific instrumentalities disclosed. The drawings are not necessarily drawn to scale. In the drawings:

FIG. 1A shows a schematic for the conjugation of a hydrazide-modified lysosomal enzyme with a benzaldehyde-modified variant IGF2 peptide. Prior to this conjugation reaction, lysosomal enzymes are chemically modified with a first crosslinking agent such as N-succinimidyl 6-hydrazinonicotinamide acetone (S-Hynic) which modifies the amino terminus and one or more lysine residues on lysosomal enzymes to introduce chemically active hydrazide functional groups. In a separate reaction, the N-terminal amino acid residue within a short extension linker region in a variant IGF2 peptide is chemically modified with a second crosslinking agent such as PEG4-pentafluorobenzyne benzoate (PEG4-PFB) to introduce a benzaldehyde function group as described in patent application. After purification of hydrazide-modified lysosomal enzymes and benzaldehyde-modified variant IGF2 peptides, these proteins are incubated together in an acidic buffer containing aniline to form IGF2 peptide-conjugated lysosomal enzymes. In this conjugation reaction, chemically active hydrazide chemical groups react with aldehyde groups to form stable covalent (hydrazone) linkages. FIG. 1B shows other suitable first crosslinking agents (succinimidyl 6-hydrazinonicotinate acetone (S-Hynic), succinimidyl 4-hydrazidoterephthalate hydrochloride (SHTH), succinimidyl 4-hydrazinium nicotinate hydrochloride (SHNH), and N-hydroxysuccinimide ester-(PEG)n-hydrazide; wherein n=3-24 PEG units) and second crosslinking agents (PEG4-pentafluorobenzyne benzoate (PEG4-PFB), succinimidyl 4-formylbenzoate (SFB), and C6-succinimidyl 4-formylbenzoate (C6-SFB)) that can be used.

FIG. 2A shows a schematic for the conjugation of phosphine-modified lysosomal enzyme with azide-modified variant IGF2 peptide via the Staudinger ligation reaction. Prior to this conjugation reaction, lysosomal enzymes are chemically modified with a first crosslinking agent such as sulfo-NHS-phosphine which modifies the amino terminus and one or more lysine residues on lysosomal enzymes to introduce chemically active phosphine functional groups. In a separate reaction, the N-terminal amino acid residue within a short extension linker region in variant IGF2 peptide is chemically modified with a second crosslinking agent such as NHS-(PEG)n-azide to introduce an azide functional group. After purification of phosphine-modified lysosomal enzymes and azide-modified variant IGF2 peptide, these proteins are incubated together in a slightly acidic buffer to form IGF2 peptide-conjugated lysosomal enzymes. In this conjugation reaction, chemically active azide chemical groups react with phosphine groups to form stable covalent (amide) linkages. FIG. 2B shows other suitable first crosslinking agents (N-hydroxysuccinimide ester-phosphine (NHS-phosphine) and Sulfo-N-hydroxysuccinimide ester-phosphine (Sulfo-NHS-phosphine) and second crosslinking agents (N-hydroxysuccinimide ester-azide (NHS-azide), N-hydroxysuccinimide ester-(PEG)n-azide; wherein n=3-24 PEG units, and NHS-PEG3-S-S-azide) that can be used.

FIG. 3A shows a schematic for the conjugation of acetylene-modified lysosomal enzyme with azide-modified IGF2 peptide via Click chemistry. Prior to this conjugation reaction, lysosomal enzymes are chemically modified with a first crosslinking agent such as NHS-(PEG)n-acetylene which modifies the amino terminus and one or more lysine residues on lysosomal enzymes to introduce chemically active acetylene functional groups. In a separate reaction, the N-terminal amino acid residue within a short extension linker region in variant IGF2 peptide is chemically modified with a second crosslinking agent such as NHS-(PEG)n-azide to introduce an azide functional group. After purification of acetylene-modified lysosomal enzymes and azide-modified IGF2 peptide, these proteins are incubated together in slightly acidic buffer with copper (I) ions to form IGF2 peptide-conjugated lysosomal enzymes. In this conjugation reaction, chemically active azide chemical groups react with alkyne groups to form stable covalent (triazole) linkages. FIG. 3B shows other suitable first crosslinking agents (N-hydroxysuccinimide ester-tetraoxapentadecane acetylene (NHS-PEG4-acetylene), N-hydroxysuccinimide ester-(PEG)n-acetylene; wherein n=3-24 PEG units, and NHS-PEG3-S-S-acetylene) and second crosslinking agents (N-hydroxysuccinimide ester-azide (NHS-azide), N-hydroxysuccinimide ester-(PEG)n-azide; wherein n=3-24 PEG units, and NHS-PEG3-S-S-azide) that can be used.

FIG. 5A shows recombinant wildtype human IGF2 peptide elutes at approximately 7.5 min corresponding to 30% acetonitrile. FIG. 5B shows recombinant variant human IGF2 peptide also elutes at approximately 7.5 min corresponding to 30% acetonitrile. FIG. 5C shows PEG4-PFB modified variant human IGF2 peptide elutes at approximately 8 min corresponding to 31% acetonitrile. These data indicate that wildtype and variant IGF2 peptides have very similar protein conformations since they behave nearly identical on C4 reverse phase chromatography. The shift in retention time for PEG4-PFB modified variant human IGF2 peptide indicates that the variant IGF2 peptide had been completely modified with the chemical crosslinker which altered its interaction on the C4 column.

DETAILED DESCRIPTION OF ILLUSTRATIVE EMBODIMENTS

Figures 4A, 4B:
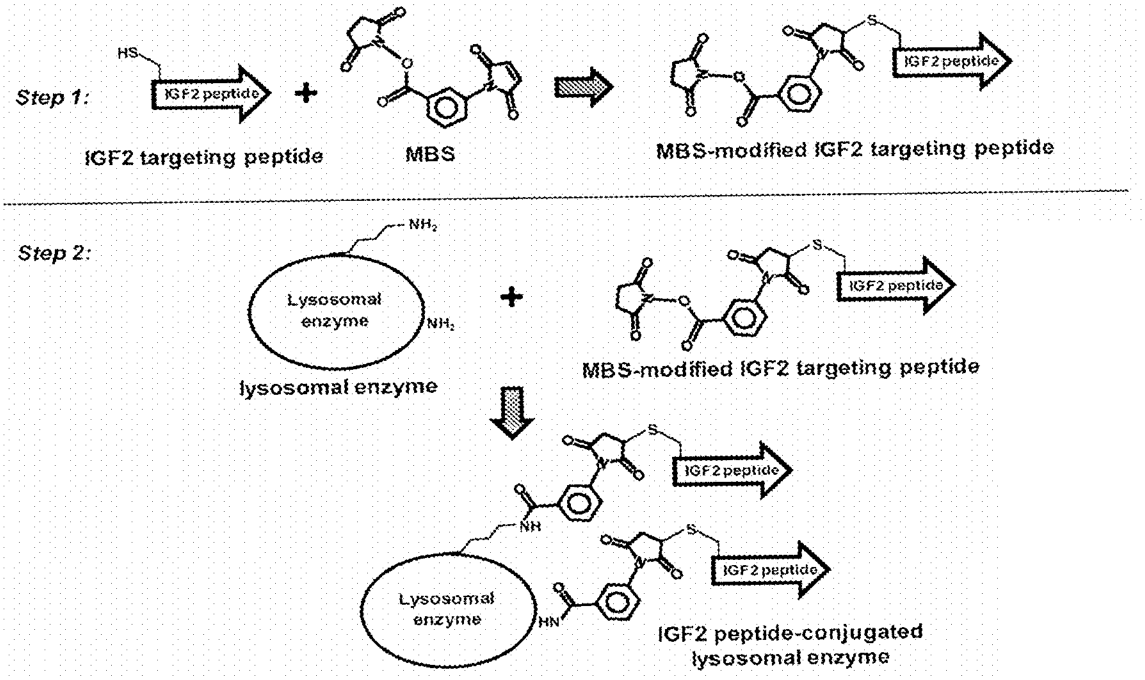
FIG. 4A shows a schematic of conjugation of lysosomal enzymes and IGF2 peptide using a single crosslinking agent such as m-maleimidobenzyol-N-hydroxysuccinimide ester (MBS). In the first reaction, the chemically reactive maleimide group reacts with the free sulfhydryl group of a C-terminal cysteine reside in a IGF2 peptide variant. The MBS-modified IGF2 peptide is then purified and then conjugated to lysosomal enzymes via crosslinking of the chemically reactive N-hydroxysuccinimide ester group with the amino terminus and one or more lysine residues on lysosomal enzymes to form stable covalent (amide) linkages.
FIG. 4B shows other suitable crosslinking agents (m-Maleimidobenzyol-N-hydroxysuccinimide ester (MBS), Sulfo-m-maleimidobenzyol-N-hydroxysuccinimide ester (sulfo-MBS), and Sulfosuccinimidyl-4-(N-maleimidomethyl)cyclohexane-1-carboxylate (SMCC)) that can be used.

The present subject matter may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention.

Also, as used in the specification including the appended claims, the singular forms “a,” “an,” and “the” include the plural, and reference to a particular numerical value includes at least that particular value, unless the context clearly dictates otherwise. The term “plurality”, as used herein, means more than one. When a range of values is expressed, another embodiment includes from the one particular value and/or to the other particular value. Similarly, when values are expressed as approximations, by use of the antecedent "about," it is understood that the particular value forms another embodiment. All ranges are inclusive and combinable.

Examples are provided to assist in a further understanding of the inventions. Particular materials used, protocols and conditions are intended to be further illustrative of the inventions and should not be construed to limit the reasonable scope thereof.

Suitable methods for conjugating a targeting peptide to a recombinant lysosomal enzyme include modifying the amino (N)-terminus and one or more lysine residues on a recombinant human lysosomal enzyme using a first crosslinking agent to give rise to a first crosslinking agent modified recombinant human lysosomal enzyme, modifying the amino (N)-terminus of a short extension linker region preceding a variant IGF-2 peptide using a second crosslinking agent to give rise to a second crosslinking agent modified variant IGF-2 peptide, and then conjugating the first crosslinking agent modified recombinant human lysosomal enzyme to the second crosslinking agent modified variant IGF-2 peptide containing a short extension linker.

Other suitable methods of conjugating a targeting peptide to a recombinant lysosomal enzyme include conjugating a first crosslinking agent modified recombinant human lysosomal enzyme to one or more second crosslinking agent modified variant IGF-2 peptides, wherein the first crosslinking agent modified recombinant lysosomal enzyme comprises a recombinant lysosomal enzyme characterized as having a chemically modified N-terminus and one or more modified lysine residues and the one or more second crosslinking agent modified variant IGF-2 peptides comprise one or more variant IGF-2 peptides comprising a modified N-terminal amino acid of a short extension linker preceding IGF2 peptide.

Suitable short extension linkers can be 5 to 20 amino acid residues in length. The short extension linker can also be about 10 amino acids in length. Suitable short extension linkers can be represented by the amino acid sequence in SEQ ID NO:3. Other suitable short extension linkers can be provided using a 5-amino acid flexible GS extension linker (glycine-glycine-glycine-glycine-serine), a 10-amino acid extension linker comprising 2 flexible GS linkers, a 15-amino acid extension linker comprising 3 flexible GS linkers, a 20-amino acid extension linker comprising 4 flexible GS linkers, or any combination thereof.

Suitable methods of making a targeting peptide conjugated to a recombinant lysosomal enzyme wherein the first crosslinking agent modified recombinant lysosomal enzyme include using a recombinant human lysosomal enzyme characterized as having a chemically modified N-terminus and one or more modified lysine residues that are modified using a first crosslinking agent. Suitable recombinant human lysosomal enzymes include human acid α-glucosidase (rhGAA), human acid α-galactosidase A (GLA), human acid β-glucuronidase (GUS), human acid α-iduronidase A (IduA), human acid iduronidate 2-sulfatase (I2S), human β-hexosaminidase A (HexA), human β-hexosaminidase B (HexB), human acid α-mannosidase A, human β-glucocerebrosidase (GlcCerase), human acid lipase (LP A), and any combinations thereof. One or more lysine residues can also be modified on the recombinant human lysosomal enzyme. Suitable first crosslinking agents include succinimidyl 6-hydrazinonicotinate acetone (S-Hynic), sulfo-succinimidyl 6-hydrazinonicotinate acetone (sulfo-S-HyNic), or C6-succinimidyl 6-hydrazino-nicotinamide (C6-S-Hynic), or succinimidyl 4-hydrazidoterephthalate hydrochloride (SHTH), or succinimidyl 4-hydrazinium nicotinate hydrochloride (SHNH) or any combination thereof to introduce hydrazide moieties on lysosomal enzymes for chemical coupling to targeting peptides that contain reactive aldehyde groups. Alternatively, lysosomal enzymes can be modified with N-hydroxysuccinimide ester-phosphine (NHS-phosphine), sulfo-NHS-phosphine, N-hydroxysuccinimide ester-tetraoxapentadecane acetylene (NHS-PEG4-acetylene) other NHS-(PEG)n-acetylene heterobifunctional crosslinkers where "n" can range from 3 to 24 discrete PEG units, or cleavable heterobifunctional crosslinkers such as NHS-PEG3-S-S-acetylene, or heterobifunctional crosslinkers containing cyclooctynes such as difluorocyclooctyne (DIFO) and dibenzocyclooctyne (DIBO) or any combination thereof for coupling chemically modified lysosomal enzymes to chemically modified targeting peptides containing reactive azide groups. Suitable second crosslinking agents for modification of targeting peptides include PEG4-pentafluorobezene-4-formylbenzoate (PEG4-PFB), or succinimidyl 4-formylbenzoate (SFB), or C6-succinimidyl 4-formylbenzoate (C6-SFB) to introduce reactive aldehyde groups onto targeting peptides for conjugation to lysosomal enzymes containing reactive hydrazide groups. Targeting peptides can also be modified with heterobifunctional crosslinkers such as N-hydroxysuccinimide ester-azide (NHS-azide) or, N-hydroxysuccinimide ester-tetraoxapentadecane-azide (NHS-PEG4-azide) or other NHS-(PEG)n-azide crosslinkers where n can range from 3 to 24 discrete PEG units, or cleavable heterobifunctional crosslinkers such as NHS-PEG3-S-S-azide, or any combination thereof to introduce reactive azide groups onto targeting peptides for conjugation to lysosomal enzymes containing reactive phosphines, or alkynes or cyclooctynes groups. In a preferred embodiment, the first crosslinking agent can be N-succinimidyl 6-hydrazinonicotinate acetone (S-Hynic) and the second crosslinking agent can be PEG4-pentafluorobezene-4-formylbenzoate (PEG4-PFB).

The N-terminus and one or more lysine residues on the recombinant human lysosomal enzyme can be modified in a buffer in the absence of primary amines at about pH 7.3 at about room temperature for about 30 minutes. The recombinant human lysosomal enzyme can be quickly exchanged into an acidic buffer after the N-terminus and lysine residues on the recombinant human lysosomal enzyme are modified. For example, the acidic buffer can be 50 mM sodium acetate, at about pH 5.0. The acidic buffer can be 0.1M sodium acetate, potassium acetate, sodium citrate, MES, sodium phosphate or potassium phosphate at about pH 5.0. The exchange into an acidic buffer can be carried out using size exclusion chromatography, and the exchange into an acidic buffer can be carried out using dialysis.

The second crosslinking agent modified variant IGF-2 peptide containing a short linker can be purified before conjugation to the first crosslinking agent modified recombinant human lysosomal enzyme. The purification can be carried out using gel filtration, dialysis or reverse phase chromatography.

The conjugation of hydrazide-modified recombinant human lysosomal enzyme to aldehyde-modified variant IGF-2 peptide containing a short linker can be carried out in acidic buffer at about pH 5.0 in the presence of aniline. The conjugation of phosphine-or acetylene- or cyclooctyne-modified recombinant human lysosomal enzyme to azide-modified variant IGF-2 peptide containing a short linker can be carried out in buffers ranging between pH 5.0-7.0. Recombinant human lysosomal enzyme-modified IGF-2 peptide containing a short linker conjugate can be purified using size exclusion chromatography or dialysis.

A suitable first crosslinking agent includes succinimidyl 6-hydrazinonicotinate acetone (S-Hynic), sulfo-succinimidyl 6-hydrazinonicotinate acetone (sulfo-S-HyNic), or C6-succinimidyl 6-hydrazino-nicotinamide (C6-S-Hynic), or succinimidyl 4-hydrazidoterephthalate hydrochloride (SHTH), or succinimidyl 4-hydrazinium nicotinate hydrochloride (SHNH) or any combination thereof to introduce hydrazide moieties on lysosomal enzymes for chemical coupling to targeting peptides that contain reactive aldehyde groups. Alternatively, lysosomal enzymes can be modified with N-hydroxysuccinimide ester-phosphine (NHS-phosphine), sulfo-NHS-phosphine, N-hydroxysuccinimide ester-tetraoxapentadecane acetylene (NHS-PEG4-acetylene) other NHS-(PEG)n-acetylene heterobifunctional crosslinkers where "n" can range from 3 to 24 discrete PEG units, or cleavable heterobifunctional crosslinkers such as NHS-PEG3-S-S-acetylene, or heterobifunctional crosslinkers containing cyclooctynes such as difluorocyclooctyne (DIFO) and dibenzocyclooctyne (DIBO) or any combination thereof for coupling these chemically modified lysosomal enzymes to targeting peptides that contain reactive azide groups. Suitable second crosslinking agents for modifying targeting peptides include PEG4-pentafluorobezene-4-formylbenzoate (PEG4-PFB), or succinimidyl 4-formylbenzoate (SFB), or C6-succinimidyl 4-formylbenzoate (C6-SFB), or N-hydroxysuccinimide ester-tetraoxapentadecane-azide (NHS-PEG4-azide), or other NHS-(PEG)n-azide heterobifunctional crosslinkers where "n" can range from 3 to 24 discrete PEG units, or cleavable heterobifunctional crosslinkers such as NHS-PEG3-S-S-azide. In another suitable embodiment, the first crosslinking agent can be N-hydroxysuccinimide ester-phosphine (NHS-phosphine) or sulfo-NHS-phosphine and the second crosslinking agent can be N-hydroxysuccinimide ester-tetraoxapentadecane-azide (NHS-PEG4-azide). In another suitable embodiment, the first crosslinking agent can be N-hydroxysuccinimide ester-tetraoxapentadecane acetylene (NHS-PEG4-acetylene) or other NHS-(PEG)n-acetylene heterobifunctional crosslinkers where "n" can range from 3 to 24 PEG units, or cleavable heterobifunctional crosslinkers such as NHS-PEG3-S-S-acetylene and the second crosslinking agent can be N-hydroxysuccinimide ester-tetraoxapentadecane-azide (NHS-PEG4-azide). In another suitable embodiment, the first crosslinking can be cyclooctynes such as difluorocyclooctyne (DIFO) and dibenzocyclooctyne (DIBO) and the second crosslinking agent can be N-hydroxysuccinimide ester-tetraoxapentadecane-azide (NHS-PEG4-azide).

The N-terminus and one or more lysine residues on the recombinant human lysosomal enzyme can be modified in a buffer lacking primary amines at about pH 7.3 at about room temperature for about 30 minutes. The recombinant human lysosomal enzyme can be quickly exchanged into an acidic buffer after the N-terminus and lysine residues on the recombinant human lysosomal enzyme are modified. A suitable acidic buffer includes 50 mM sodium acetate, at about pH 5.0. The acidic buffer can be 0.1M sodium acetate, potassium acetate, sodium citrate, MES, sodium phosphate or potassium phosphate at about pH 5. The exchange into an acidic buffer can be suitably carried out using size exclusion chromatography or using dialysis.

The second crosslinking agent modified variant IGF-2 peptide containing a short linker before can be purified prior to conjugation to the first crosslinking agent modified recombinant human lysosomal enzyme using gel filtration, dialysis or reverse phase chromatography. The conjugation of hydrazide-modified recombinant human lysosomal enzyme to aldehyde-modified variant IGF-2 peptide containing a short linker can be carried out in acidic buffer at about pH 5.0 in the presence of aniline. The conjugation of phosphine- or acetylene- or cyclooctyne-modified recombinant human lysosomal enzyme to azide-modified variant IGF-2 peptide containing a short linker can be carried out in buffers ranging between pH 5.0-7.0. Recombinant human lysosomal enzyme-modified IGF-2 peptide containing a short linker conjugate can be purified using size exclusion chromatography or dialysis.

After conjugation, the recombinant human lysosomal enzyme-variant IGF-2 peptide containing a short linker can be purified using size exclusion chromatography or dialysis.

The conjugation of the first crosslinking agent (HS-PEG4-acetylene) modified recombinant human lysosomal enzyme to the second crosslinking agent (HS-PEG4-azide) modified variant IGF-2 peptide containing a short linker in acidic buffer at about pH 5.0 can be carried out in the presence of copper ($Cu^{+1}$). Following this conjugation step, a purification step of the recombinant human lysosomal enzyme-modified IGF-2 peptide containing a short linker conjugate can be carried out using size exclusion chromatography or dialysis.

The conjugation of the first crosslinking agent (cyclooctyne such as difluorocyclooctyne; DIFO) modified recombinant human lysosomal enzyme to the second crosslinking agent (HS-PEG4-azide) modified variant IGF-2 peptide containing a short linker in acidic buffer at about pH 6.0. Following this conjugation step, a purification step of the recombinant human lysosomal enzyme-modified IGF-2 peptide containing a short linker conjugate can be carried out using size exclusion chromatography or dialysis.

Molecules for enzyme replacement therapy can be generated by conjugating a heterobifunctional crosslinking agent to a variant IGF-2 peptide and then conjugating the heterobifunctional crosslinking agent modified variant IGF-2 peptide to a recombinant human lysosomal enzyme. Molecule for enzyme replacement therapy can also be made by conjugating a heterobifunctional crosslinking agent to a recombinant human lysosomal enzyme and then conjugating the heterobifunctional crosslinking agent modified recombinant human lysosomal enzyme to a variant IGF-2 peptide. Suitable recombinant human lysosomal enzymes include human acid α-glucosidase (rhGAA), human acid β-galactosidase A (GLA), human acid β-glucuronidase (GUS), human acid α-iduronidase A (IduA), human acid iduronidate 2-sulfatase (I2S), human β-hexosaminidase A (HexA), human β-hexosaminidase B (HexB), human acid α-mannosidase A, human β-glucocerebrosidase (GlcCerase), human acid lipase (LPA), or any combination thereof. Suitable heterobifunctional crosslinking agents include m-maleimidobenzyol-N-hydroxysuccinimide ester (MBS), Sulfo-m-maleimidobenzyol-N-hydroxysuccinimide ester (sulfo-MBS) or any combination thereof. The variant IGF-2 peptide-recombinant human lysosomal enzyme conjugate can be optionally purified using gel filtration or dialysis.

Suitable recombinant human lysosomal enzymes can be made using yeast. The recombinant human lysosomal enzyme made from yeast can be treated using endoglycosidase F (EndoF) or endoglycosidase H (EndoH) to remove N-glycans. In another suitable embodiment, treatment using endoglycosidase F (EndoF) or endoglycosidase H (EndoH) can occur in acidic pH buffer. Suitable acidic pH buffers include 0.1M sodium acetate, pH 5.0. The reactions can be carried out at about room temperature. After treatment using endoglycosidase F (EndoF) or endoglycosidase H (EndoH) the recombinant human lysosomal enzyme can optionally be purified using size exclusion chromatography or dialysis.

Conjugates of one or more variant IGF-2 peptides chemically linked to a recombinant human lysosomal enzyme are also provided. In these embodiments, the first crosslinking agent modified recombinant lysosomal enzyme can be a recombinant human lysosomal enzyme, and the recombinant human lysosomal enzyme can have one or more modified lysine residues, for example the N-terminus can be chemically modified. Suitable variant IGF-2 peptides can be an IGF-2 peptide analog and a short linker with at the N-terminus. At least one of the variant IGF-2 peptides is suitably an IGF-2 peptide that has a modified N-terminus within a short linker. A suitable modified IGF-2 peptide is characterized as being capable of being modified at the N-terminus in a buffer at about pH 7.5. Suitable variant IGF-2 peptides include a synthetic IGF-2 peptide analog, containing a short linker at the N- or C-terminus with the appropriate reactive chemical group. Suitable variant IGF-2 peptides comprise an IGF-2 peptide analog, a short linker at the N-terminus can be generated as a recombinant protein and the N-terminal amino acid can be subsequently chemically modified with bifunctional crosslinkers.

A suitable recombinant human lysosomal enzyme includes a human acid α-glucosidase (rhGAA). Other suitable recombinant human lysosomal enzymes that can be used in these methods include human acid α-galactosidase A (GLA), human acid β-glucuronidase (GUS), human acid α-iduronidase A (IduA), human acid isuronidate 2-sulfatase (I2S), human β-hexosaminidase A (HexA), human β-hexosaminidase B (HexB), human acid α-mannosidase A, human β-glucocerebrosidase (GlcCerase), human acid lipase (LPA), or any combination thereof. Suitable recombinant human lysosomal enzymes are characterized as having a modified N-terminus and at least one modified lysine residue.

Suitable first crosslinking agent modified recombinant lysosomal enzymes can be characterized as having a crosslinking agent derived from an amino-reactive bifunctional crosslinker. A suitable first crosslinking agent modified recombinant lysosomal enzyme can be characterized as comprising a crosslinking agent derived from succinimidyl 6-hydrazinonicotinate acetone (S-Hynic), sulfo-succinimidyl 6-hydrazinonicotinate acetone (sulfo-S-HyNic), or C6-succinimidyl 6-hydrazino-nicotinamide (C6-S-Hynic), or succinimidyl 4-hydrazidoterephthalate hydrochloride (SHTH), or succinimidyl 4-hydrazinium nicotinate hydrochloride (SHNH) or any combination thereof to introduce hydrazide moieties. Alternatively, lysosomal enzymes can be modified with N-hydroxysuccinimide ester-phosphine (NHS-phosphine), sulfo-NHS-phosphine, N-hydroxysuccinimide ester-tetraoxapentadecane acetylene (HS-PEG4-acetylene) other NHS-(PEG)n-acetylene heterobifunctional crosslinkers where “n” can range from 3 to 24 discrete PEG units, or cleavable heterobifunctional crosslinkers such as NHS-PEG3-S-S-acetylene, or heterobifunctional crosslinkers containing cyclooctynes such as difluorocyclooctyne (DIFO) and dibenzocyclooctyne (DIBO) or any combination thereof for coupling these chemically modified lysosomal enzymes to targeting peptides that contain reactive azide groups. The modified N-terminus and lysine residues on the recombinant human lysosomal enzyme can be characterized as being derived from the primary amine on the first (N-terminal) amino acid and lysine residues modified in a buffer lacking primary amines at about pH 7.3 at about room temperature for about 30 minutes. Variant IGF-2 peptides can also include the IGF-2 peptide and a short extension linker coupled to a second crosslinking agent. A suitable second crosslinking agent can be PEG4-pentafluorobezene-4-formylbenzoate (PEG4-PFB) for conjugation to succinimidyl 6-hydrazinonicotinate acetone (S-Hynic)-modified lysosomal enzymes. In a different embodiment, the second crosslinking agent can comprise NHS-PEG4-azide for conjugation to phosphine-modified lysosomal enzymes. In another embodiment, the second crosslinking agent can comprise N-hydroxysuccinimide ester-PEG4-azide (NHS-PEG4-azide) for conjugation to acetylene-modified lysosomal enzymes. In yet another embodiment, the second crosslinker can comprise N-hydroxysuccinimide ester-PEG4-azide (NHS-PEG4-azide) for conjugation to cyclooctyne-modified lysosomal enzyme.

A heterobifunctional crosslinking agent modified variant IGF-2 peptide conjugated to a recombinant human lysosomal enzyme is also provided. Suitable heterobifunctional crosslinking agent modified variant IGF-2 peptides are characterized as being derived from a heterobifunctional crosslinking agent conjugated to a variant IGF-2 peptide. A suitable recombinant human lysosomal enzyme can be human acid α-glucosidase (rhGAA), human acid α-galactosidase A (GLA), human acid β-glucuronidase (GUS), human acid α-iduronidase A (IduA), human acid iduronidate 2-sulfatase (I2S), human β-hexosaminidase A (HexA), human β-hexosaminidase B (HexB), human acid α-mannosidase A, human β-glucocerebrosidase (GlcCerase), human acid lipase (LPA). A suitable heterobifunctional crosslinking agent includes m-maleimidobenzyol-N-hydroxysuccinimide ester (MBS and sulfo-m-maleimidobenzyol-N-hydroxysuccinimide ester (sulfo-MBS), Sulfosuccinimidyl-4-(N-maleimidomethyl)cyclohexane-1-carboxylate (sulfo-SMCC). The conjugates can be substantially pure with less than 10 percent of free, unconjugated IGF2 peptide. The purity of the conjugate can be measured by absorbance with lysosomal protein at 280 nm and free IGF2 peptide at 214 nm in fractions from size exclusion chromatography or by stained protein gels using sodium docecylsulfate polyacrylamide gel electrophoresis (SDS-PAGE) or by Western blotting after SDS-PAGE and specific antibodies for detection of lysosomal enzymes or IGF2 peptide. The conjugate can also be substantially pure with less than 0.1 percent of free, unconjugated IGF2 peptide or other contaminants. The recombinant human lysosomal enzyme can be suitably derived from yeast with high-mannose or complex-type N-glycans. Suitable recombinant human lysosomal enzymes derived from yeast with complex-type N-glycans can be used directly for conjugation to IGF2 peptide. Suitable recombinant human lysosomal enzymes with high-mannose type N-glycans can also be treated using endoglycosidase F (EndoF) or endoglycosidase H (EndoH) to remove these exotic N-glycans prior to or after chemical conjugation. The recombinant human lysosomal enzyme can be suitably derived from other protein expression systems including insect cells, plant cells, fungi, transgenic animals and in vitro translation systems.

Methods for treating a subject suffering from a lysosomal storage disease are carried out by administering to the subject a conjugate of one or more variant IGF-2 peptides chemically conjugated to a chemically modified recombinant human lysosomal enzyme. Any of a variety of lysosomal storage diseases can be treated this way, including at least one of the following diseases: Pompe Disease, Fabry Disease, and Gaucher Disease, MPS I, MPSII, MPS VII, Tay Sachs, Sandhoff, α-mannosidosis, and Wohlman.

Methods for treating a subject suffering from a lysosomal storage disease are carried out by administering to the subject a conjugate of a heterobifunctional crosslinking agent modified variant IGF-2 peptide conjugated to a recombinant human lysosomal enzyme. Any of a variety of lysosomal storage diseases can be treated this way, including at least one of the following diseases: Pompe Disease, Fabry Disease, and Gaucher Disease, MPS I, MPSII, MPS VII, Tay Sachs, Sandhoff, α-mannosidosis, and Wohlman.

Methods of treating a patient suffering from Pompe, Fabry, Gaucher, MPS I, MPSII, MPS VII, Tay Sachs, Sandhoff, α-mannosidosis, or Wohlman disease is also provided by administering to a patient in need thereof, a composition of one or more variant IGF-2 peptides chemically conjugated to a recombinant lysosomal enzyme and a pharmaceutically acceptable carrier, in an amount sufficient to treat the disease. A suitable modified recombinant human lysosomal enzyme includes acid α-glucosidase for the treatment of Pompe disease. The modified recombinant human lysosomal enzyme can also be acid α-galactosidase A for the treatment of Fabry disease. The modified recombinant human lysosomal enzyme can be acid β-glucocerebrosidase for the treatment of Gaucher disease. The modified recombinant human lysosomal enzyme can be acid α-iduronidase for the treatment of mucopolysaccharidosis I (MPS I). The modified recombinant human lysosomal enzyme can be acid iduronidate 2-sulfatase for the treatment of mucopolysaccharidosis II (MPS II). The modified recombinant human lysosomal enzyme can also be acid β-glucuronidase for the treatment of mucopolysaccharidosis VII (MPS VII). Alternatively, the modified recombinant human lysosomal enzyme can be β-hexosaminidase A for the treatment of GM2 gangliosidoses (Tay-Sachs). In another suitable embodiment the modified recombinant human lysosomal enzyme can be β-hexosaminidase B for the treatment of GM2 gangliosidoses (Sandhoff). In another embodiment the modified recombinant human lysosomal enzyme can be acid lipase for the treatment of Wohlman disease. The modified recombinant human lysosomal enzyme can also be acid α-mannosidase for the treatment of α-mannosidosis. The compositions provided herein can be administered in an amount of from about 0.1 to about (100 milligrams of one or more variant IGF-2 peptides chemically conjugated to a recombinant lysosomal enzyme per patient kilogram per month. In another suitable embodiment the composition can be administered in an amount of from about 1 to about 500 milligrams of one or more variant IGF-2 peptides chemically conjugated to a recombinant lysosomal enzyme per patient per kilogram per month.

Methods of treating a patient suffering from Pompe, Fabry, Gaucher, MPS I, MPS II, MPS VII, Tay Sachs, Sandhoff, α-mannosidosis, Wohlman disease are also provided by administering to a patient in need thereof, a composition of a heterobifunctional crosslinking agent modified variant IGF-2 peptide conjugated to a recombinant human lysosomal enzyme and a pharmaceutically acceptable carrier, in an amount sufficient to treat the disease. The composition can be administered in an amount of from about 0.1 to about 1000 milligrams of a heterobifunctional crosslinking agent modified variant IGF-2 peptide conjugated to a recombinant human lysosomal enzyme per 50 kilograms of patient per month. In another suitable embodiment, the composition can be administered in an amount of from about 1 to about 500 milligrams of a heterobifunctional crosslinking agent modified variant IGF-2 peptide conjugated to a recombinant human lysosomal enzyme per 50 kilograms of patient per month.

A suitable DNA sequence that encodes a variant IGF-2 peptide that is optimized for expression in *E. coli* is provided as SEQ ID NO: 1. A suitable amino acid sequence that represents a variant IGF-2 peptide is provided as SEQ ID NO: 2. A suitable amino acid sequence that represents an extension linker is provided as SEQ ID NO: 3. The variant IGF2 peptide used in the methods can have the amino acid sequence of SEQ ID NO: 2. In another embodiment the variant IGF2 peptide in the conjugates can have the amino acid sequence of SEQ ID NO: 2.

EXAMPLES AND OTHER ILLUSTRATIVE EMBODIMENTS

A chemical crosslinking method is employed to conjugate variant human IGF-2 peptides to lysosomal enzymes for developing novel and superior ERTs for the treatment of various lysosomal storage disorders (LSDs). This strategy is expected to increase the binding affinity of IGF2 peptide-conjugated ERTs for the IGF-2/CI-MPR and improve cellular uptake and delivery of these recombinant enzymes to lysosomes. By doing so, these IGF2 peptide-conjugated ERTs are expected to be more effective in clearing accumulated substrate in affected cells.

Several different variants of human IGF-2 peptides can be synthesized or expressed (in mammalian cells or in other organisms), purified and subsequently chemically modified with heterobifunctional crosslinkers for conjugation to lysosomal enzymes. A variant IGF-2 peptide can contain one or combinations of following modifications: substitution of arginine for glutamic acid at position 6; deletion of amino acids 1-4 and 6; deletion of amino acids 1-4 and 6, 7; deletion of amino acids 1-4 and 6 and substitution of lysine for threonine at position 7; deletion of amino acids 1-4 and substitution of glycine for glutamic acid at position 6 and substitution of lysine for threonine at position 7; substitution of leucine for tyrosine at position 27; substitution of leucine for valine at position 43; substitution of arginine for lysine at position 65. The majority of these modifications are designed to reduce binding affinity of IGF-2 peptides for the insulin and IGF-1 receptors and for serum IGF binding proteins (IGFBPs) while maintaining high affinity for the IGF-2/CI-MPR. The modified IGF-2 peptides may also contain an affinity tag (e.g., polyhistidine; His tag) for rapid purification of the modified IGF-2 peptide, may be expressed as fusion proteins with soluble protein partners, a protease site (e.g., enhanced tobacco etch virus (TEV) protease site) for removal of the affinity tag or fusion protein partner, a linker extension region of at least five amino acids preceding IGF-2.

Variant IGF-2 peptides and recombinant lysosomal enzymes can be chemically coupled by two primary strategies. (A) Independently modify the IGF-2 peptide with a heterobifunctional crosslinker and the recombinant lysosomal enzyme with a different heterobifunctional crosslinker (as described in examples 1-3). After purification to remove excess, unconjugated crosslinker and chemical byproducts, the chemically-modified IGF2 peptide and chemically-modified lysosomal enzyme are subsequently conjugated together in a final chemical reaction to form the IGF2 peptide-lysosomal enzyme conjugate and purified and stored in an acidic pH buffer to maintain enzyme activity. (B) Chemically conjugate the IGF2 peptide and lysosomal enzyme using a single heterobifunctional crosslinker (as described in example 4). The IGF-2 peptide is chemically modified with the heterobifunctional crosslinker at one pH reaction condition. The chemically modified lysosomal enzyme is then added and the pH adjusted to a second pH reaction condition to conjugate the IGF2 peptide to lysosomal enzyme. The conjugate is then be purified to remove excess, unconjugated heterobifunctional crosslinker and chemical byproducts and stored in an acidic pH buffer to maintain enzyme activity.

The above chemical coupling approach has distinct advantages for improving protein targeting for lysosomal enzyme replacement therapies. First, conjugation of modified IGF-2 peptides increases binding affinity of lysosomal enzymes for the IGF-2/CI-MPR without requiring specialized M6P carbohydrate structures. Second, unlike IGF-2 fusion proteins which contains a single IGF-2 peptide per lysosomal enzyme, this strategy can append multiple modified IGF-2 peptides to lysosomal enzymes for higher affinity for the IGF-2/CI-MPR. Third, this approach can be used to conjugate mixed peptides (IGF2 peptide and other peptides) for improving drug targeting to other tissues (e.g., the brain). Fourth, this approach can utilize recombinant lysosomal enzymes produced from most eukaryotic expression systems including but not limited to mammalian cells, yeast, insect cells, plant cells, transgenic animals (e.g., in hen eggs, milk, etc.). Recombinant lysosomal enzymes that contain complex-type N-glycans (i.e., derived from mammalian expression systems, yeast with modified N-glycan processing that yield complex N-glycans, transgenic animals, etc.) can be directly utilized for coupling. Enzymes bearing high-mannose type N-glycans (i.e., derived from yeast, Lec1 mammalian cell lines, etc.) can be subjected to deglycosylation (via endoglycosidases such as EndoF or EndoH) prior to or after chemical coupling to modified IGF-2 peptides (as described in example 5). Fifth, modified IGF-2 peptides can be manufactured in most expression systems including bacteria, yeast or other fungal systems which enable a cost-effective approach for scale up of process. Sixth, the same modified IGF-2 peptides can be conjugated to any lysosomal enzyme to improve protein targeting without having to create individual fusion proteins of IGF2-lysosomal enzyme. Seventh, this strategy can create novel, superior ERT compositions that potentially could reduce drug requirements, decrease infusion time and reduce immunogenicity.

Example 1

Recombinant human acid α-glucosidase (rhGAA) derived from most mammalian cell manufacturing systems contain very low amounts of M6P with mostly complex-type N-glycans that are not adequate for high affinity binding of rhGAA to the IGF-2/CI-MPR. This N-glycan profile resembles that for serum proteins and thus, enables rhGAA to have a favorable pharmacokinetic profile (i.e., slower clearance) in the circulation. rhGAA can therefore be utilized for conjugation to modified IGF-2 peptides to increase its affinity for the IGF-2/CI-MPR for improved protein targeting and cellular uptake to develop a superior rhGAA ERT. Specifically, rhGAA can be concentrated to a protein concentration of 8-10 mg/ml and exchanged into buffers at about pH 7.3 lacking primary amines (e.g., 50 mM sodium phosphate, pH 7.3/100 mM NaCl) and subsequently modified with a 12- to 20-fold molar excess of the heterobifunctional crosslinker succinimidyl 6-hydrazinonicotinate acetone (S-Hynic) at room temperature for about 30 min. In this reaction, the chemically reactive N-hydroxysuccinimide ester (NHS) group from S-Hynic reacts with the α-amino group of the first amino acid residue at the amino (N)-terminus and ε-amino groups of lysines on rhGAA to introduce novel, chemically active hydrazide groups at these modified amino acid residues. The S-Hynic-modified rhGAA then quickly exchanges into acidic buffer (e.g., 50 mM NaOAc, pH 4.8/100 mM NaCl/0.05% Polysorbate-80) via size exclusion chromatography or dialysis to remove excess crosslinker and chemical byproducts and to preserve enzymatic activity. This chemical reaction can be titrated with varying amounts of S-Hynic (e.g., 5-40× molar excess) to understand the ratio of S-Hynic to rhGAA that reproducibly yields 1-4 chemically-active hydrazide groups on rhGAA. The optimal conditions are then used for scaling up the S-Hynic modification reaction of rhGAA.

Figures 5A, 5B, 5C:
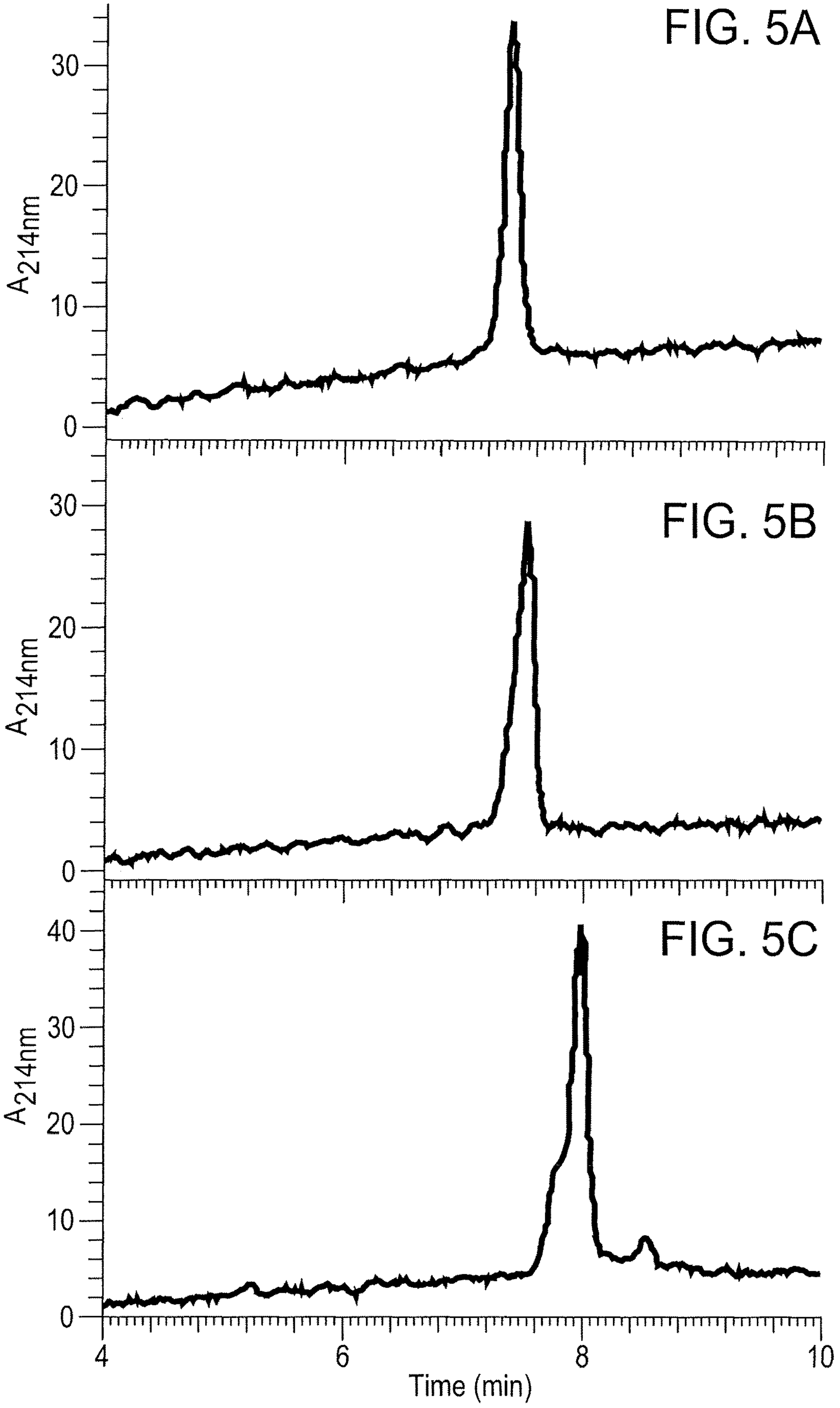
FIGS. 5A-5C show characterization of IGF2 peptides by C4 reverse phase chromatography. A 4.6×150 mm C4 reverse phase analytical column was utilized for evaluating the purity and protein conformation of wildtype and variant IGF2 peptides. Peptide samples were loaded onto C4 column equilibrated with 0.1% trifluoracetic acid (TFA) and 25% acetonitrile. After 2 minutes, the column was developed using a 25-35% acetonitrile linear gradient over a 10 min.

In a separate reaction, a variant IGF2 peptide such as [del(1-4), Arg6, Leu27, Arg65] IGF-2 containing a short extension linker region (at N-terminus), is chemically modified using the heterobifunctional crosslinker PEG4-pentafluorobezene-4-formylbenzoate (PEG4-PFB) at pH~7.5, room temperature for 2-3 hours. In this reaction, the PEG4-PFB modifies the α-amino group of the first amino acid glycine from the short extension linker region to introduce a novel reactive aldehyde chemical group at the amino terminus. The chemical modification of variant IGF2 peptide can be monitored by C4 reverse phase chromatography to assess the progression and completeness of chemical modification as shown in FIGS. 5A-5C. The PEG4-benzaldehyde-modified IGF-2 peptide is then purified by gel filtration chromatography or dialysis to remove excess crosslinker and chemical byproducts in an appropriate buffer for conjugation (e.g., 50 mM NaOAc, pH 4.8/100 mM NaCl/0.05% Polysorbate-80). A final reaction is then performed to conjugate the S-Hynic-modified rhGAA to the PEG4-benzaldehyde-modified IGF-2 peptide in 50 mM NaOAc, pH 4.8/100 mM NaCl/0.05% Polysorbate-80 buffer over a 24 hr period at room temp. This chemistry couples the hydrazide groups from the S-Hynic-modified rhGAA to chemically-active aldehyde groups from PEG4-benzaldehyde-modified IGF2 peptides to form stable covalent (hydrazone) bonds. This reaction can be performed in the presence of aniline (e.g., 10 mM) with varying amounts of PEG4-benzaldehyde-modified IGF-2 peptide (e.g., 1-10× molar excess) to optimize coupling. The IGF-2 peptide-conjugated rhGAA is then purified by size exclusion chromatography or dialysis against 50 mM sodium phosphate, pH 6.2/100 mM NaCl/0.05% Polysorbate-80 to remove excess PEG4-benzaldehyde-modified IGF-2 peptides and the variant IGF2 peptide-conjugated rhGAA (vIGF2-rhGAA) is stored in the same buffer at 4° C. or frozen at −20° C. or −70° C.

Example 2

Recombinant human acid α-glucosidase (rhGAA) derived from mammalian manufacturing systems are utilized for conjugation to variant IGF-2 peptides to increase affinity for the IGF-2/CI-MPR for improved protein targeting and cellular uptake to develop a superior rhGAA ERT. Specifically, the Staudinger Ligation (azide-phosphine) reaction chemistry is used to couple IGF2 peptides to rhGAA to generate an IGF2 peptide-rhGAA conjugate for improved drug targeting. In this example, rhGAA (at 5-10 mg/ml) is exchanged into buffers at about pH 7.3 lacking primary amines (e.g., 50 mM sodium phosphate (pH 7.3)/00) mM NaCl) and subsequently is modified with 10- to 20-fold molar excess of the heterobifunctional crosslinker sulfo-N-hydroxysuccinimide ester-phosphine (sulfo-NHS-phosphine) at room temperature for about 30 min. In this chemical reaction, the chemically reactive NHS group from sulfo-NHS-phosphine reacts with the α-amino group of the first amino acid residue at the N-terminus and ε-amino groups of lysines on rhGAA to introduce novel, chemically active phosphine groups at these modified amino acid residues. The phosphine-containing rhGAA is then quickly exchanged into slightly acidic buffer (e.g., 50 mM sodium phosphate, pH 6.5/100 mM NaCl) via size exclusion chromatography or dialysis to remove excess crosslinker and chemical byproducts and to preserve enzymatic activity. This chemical reaction can be titrated with varying amounts of sulfo-NHS-phosphine (e.g., 5-40× molar excess) to understand the ratio of sulfo-NHS-phosphine to rhGAA that reproducibly yields 1-4 chemically-active phosphine groups on rhGAA. The optimal conditions can be used for scaling up the sulfo-NHS-phosphine modification reaction of rhGAA.

In a separate reaction, a variant IGF-2 peptide such as [del(1-4), Arg6, Leu27, Arg65] IGF-2 containing a short extension linker region (at N-terminus), is chemically modified using a 30-fold molar excess of the heterobifunctional crosslinker N-hydroxysuccinimide ester-PEG4-azide (NHS-PEG4-azide) in a pH~7.5 buffer lacking primary amines (e.g., 50 mM sodium phosphate/50 mMNaCl, pH 7.5) at room temp for 1-3 hrs. In this reaction, the reactive NHS group of NHS-PEG4-azide is reacted with the α-amino group of glycine from the short extension linker region to introduce a novel azide chemical group at the N-terminus. The chemical modification of variant IGF2 peptide can be monitored by C4 reverse phase chromatography to assess the progression and completeness of chemical modification. The PEG4-azide-modified IGF-2 peptide is then purified by C4 reverse phase chromatography and the modified peptide is lyophilized to remove solvents and stored as a dry powder.

A final reaction is then performed to conjugate the phosphine-modified rhGAA to the PEG4-azide-modified IGF-2 peptide by directly adding phosphine-modified rhGAA (in 50 mM sodium phosphate, pH 6.5/100 mM NaCl buffer) to the freeze dried PEG4-azide-modified IGF-2 peptide at a molar ratio of 1 part rhGAA to 5 parts IGF2 peptide with incubation at room temp over a 24 hr period. This chemistry couples the azide chemical group from the azide-modified IGF-2 peptide to phosphine-modified rhGAA to form stable covalent (amide) bonds. The variant IGF-2 peptide-conjugated rhGAA (vIGF2-rhGAA) is then purified by size exclusion chromatography or dialysis to remove excess PEG4-azide-modified IGF-2 peptides and stored in slightly acidic pH buffer (50 mM sodium phosphate, pH 6.5/100 mM NaCl buffer) at 4° C.

Example 3

Recombinant human acid iduronidate 2-sulfatase (I2S) derived from mammalian manufacturing systems is utilized for conjugation to variant IGF-2 peptides to increase enzyme affinity for the IGF-2/CI-MPR for improved protein targeting and cellular uptake to develop a superior I2S ERT. Specifically, the Staudinger Ligation (azide-phosphine) reaction chemistry is used to couple variant IGF2 peptides to I2S to generate an IGF2 peptide-I2S conjugate for improved drug targeting. In this example, I2 S (at approximately 3 mg/ml) is modified with 20-fold molar excess of the heterobifunctional crosslinker sulfo-N-hydroxysuccinimide ester-phosphine (sulfo-NHS-phosphine) in a pH~7.3 buffer lacking primary amines (e.g., 50 mMM sodium phosphate/100 mM NaCl, pH 7.3) at room temperature for about 30 min. In this chemical reaction, the chemically reactive NHS group from sulfo-NHS-phosphine reacts with the α-amino group of the first amino acid residue at the N-terminus and ε-amino groups of lysines on I2S to introduce novel, chemically active phosphine groups at these modified amino acid residues. The phosphine-containing I2S is then quickly exchanged into slightly acidic buffer (e.g., 50 mM sodium phosphate, pH 6.5/100 mM NaCl) via size exclusion chromatography or dialysis to remove excess crosslinker and chemical byproducts and to preserve enzymatic activity. This chemical reaction can be titrated with varying amounts of sulfo-NHS-phosphine (e.g., 5-40× molar excess) to understand the ratio of sulfo-NHS-phosphine to I2S that reproducibly yields 1-4 chemically-active phosphine groups on I2S. The optimal conditions can be used for scaling up the sulfo-NHS-phosphine modification reaction of I2S.

In a separate reaction, a variant IGF-2 peptide such as [del(1-4), Arg6. Leu27, Arg65] IGF-2 containing a short extension linker region (at N-terminus), is chemically modified using a 30-fold molar excess of the heterobifunctional crosslinker N-hydroxysuccinimide ester-PEG4-azide (NHS-PEG4-azide) in a pH~7.5 buffer lacking primary amines (e.g., 50 mM sodium phosphate/50 mMNaCl, pH 7.5) at room temp for 1-3 hrs. In this reaction, the reactive NHS group of NHS-PEG4-azide is reacted with the α-amino group of glycine from the short extension linker region to introduce a novel azide chemical group at the N-terminus. The chemical modification of variant IGF2 peptide can be monitored by C4 reverse phase chromatography to assess the progression and completeness of chemical modification. The PEG4-azide-modified IGF-2 peptide is then purified by C4 reverse phase chromatography and the peptide is lyophilized and stored as a dry powder.

A final reaction is then performed to conjugate the phosphine-modified I2 S to the PEG4-azide-modified IGF-2 peptide by directly adding phosphine-modified I2S (in 50 mM sodium phosphate, pH 6.5/100 mM NaCl buffer) to the freeze dried PEG4-azide-modified IGF-2 peptide at a molar ratio of 1 part I2 S to 5 parts IGF2 peptide with incubation at room temp over a 24 hr period. This chemistry couples the reactive azide chemical group from the azide-modified IGF-2 peptide to phosphine-modified I2S to form stable covalent (amide) bonds. The variant IGF-2 peptide-conjugated I2S (vIGF2-I2S) is then purified by size exclusion chromatography or dialysis to remove excess PEG4-azide-modified IGF-2 peptides and stored in slightly acidic pH buffer (50 mM sodium phosphate, pH 6.5/100 mM NaCl buffer) at 4° C.

Example 4

Recombinant human acid α-glucosidase (rhGAA) derived from mammalian manufacturing systems will be utilized for conjugation to modified IGF-2 peptides to increase affinity for the IGF-2/CI-MPR for improved protein targeting and cellular uptake to develop a superior rhGAA ERT. In this example, a variant IGF2 peptide such as [del(1-4), Arg6, Leu27, Arg65] IGF-2 containing a short extension linker region with a cysteine residue at the N-terminus is modified with the heterobifunctional crosslinker m-maleimidobenzyol-N-hydroxysuccinimide ester (MBS) at about pH 6 and room temp for 30-60 min. In this reaction, the chemically reactive maleimide group from MBS will react with the free sulfhydryl group from the N-terminal cysteine while preserving the N-hydroxysuccinimide ester reactive group for coupling to rhGAA. The MBS-modified IGF-2 peptide will be quickly purified by gel filtration chromatography or dialysis to remove excess MBS. rhGAA is then added for coupling to the MBS-modified IGF-2 peptide at room temp in non-amine containing buffer at pH 7.3 for 30 min. In this chemical reaction, the chemically reactive N-hydroxysuccinimide ester group (from MBS-modified IGF-2 peptide) reacts with the α-amino group of the first amino acid residue at the N-terminus and ε-amino groups of lysines on rhGAA to form stable covalent linkages. This reaction will be titrated using varying amounts of MBS-modified IGF-2 peptide (e.g., 1-20× molar excess) to determine the molar excess of MBS-modified IGF-2 peptide to couple 1-4 IGF-2 peptides on rhGAA. The optimal coupling conditions are then used for scaling up this process. The IGF-2-conjugated rhGAA will be purified by gel filtration chromatography or dialysis to remove excess IGF-2 peptides and stored in acidic pH buffer (0.1M sodium citrate, pH 5.5 buffer).

Example 5

Recombinant human lysosomal enzymes such as rhGAA with high-mannose type N-glycan structures (derived from yeast, GNT-1 deficient Led mammalian cells, etc.) can be utilized for conjugation to variant IGF-2 peptides to increase affinity for the IGF-2/CI-MPR for improved protein targeting and cellular uptake to develop a superior rhGAA ERT. In this example, rhGAA (at 8-10 mg/ml) is exchanged into buffers at about pH 7.3 lacking primary amines (e.g., 50 mM sodium phosphate (pH 7.3)/100 mM NaCl) and subsequently modified with a heterobifunctional crosslinker such as N-succinimidyl 6-hydrazinonicotinate acetone (S-Hynic) in a pH~7.3 buffer lacking primary amines (e.g., 50 mM sodium phosphate/0.1 M NaCl, pH 7.3) at room temperature for 30 min. The hydrazide-modified rhGAA is then quickly exchanged into acidic buffer (e.g., 50 mM NaOAc, pH 4.8/100 mM NaCl/0.05% Polysorbate-80) via size exclusion chromatography or dialysis to remove excess crosslinker and chemical byproducts and to preserve enzymatic activity.

In a separate reaction, a variant IGF-2 peptide such as [del(1-4), Arg6, Leu27, Arg65] IGF-2 containing a short extension linker region (at N-terminus), is chemically modified using a 30-fold molar excess of the heterobifunctional crosslinker PEG4-pentafluorobezene-4-formylbenzoate (PEG4-PFB) in a pH~7.5 buffer lacking primary amines (e.g., 50 mM sodium phosphate/50 mM NaCl, pH 7.5) at room temp for 1-3 hrs. In this reaction, PEG4-PFB modifies the α-amino group of glycine from the short extension linker region to introduce a novel aldehyde chemical group at the N-terminus. The chemical modification of variant IGF2 peptide can be monitored by C4 reverse phase chromatography to assess the progression and completeness of chemical modification. The PEG4-benzaldehyde-modified IGF-2 peptide is then purified by gel filtration chromatography or dialysis to remove excess crosslinker and chemical byproducts in an appropriate buffer for conjugation (e.g., 50 mM NaOAc, pH 4.8/100 mM NaCl/0.05% Polysorbate-80).

A final reaction is then performed to conjugate the S-Hynic-modified rhGAA to the PEG4-benzaldehyde-modified IGF-2 peptide in 50 mM NaOAc, pH 4.8/100 mM NaCl/0.05% Polysorbate-80 buffer over a 24 hr period at room temp. This chemistry couples the hydrazide groups from the S-Hynic-modified rhGAA to chemically-active aldehyde groups from PEG4-benzaldehyde-modified IGF2 peptides to form stable covalent (hydrazone) bonds. This reaction can be performed in the presence of aniline (e.g., 10 mM) with varying amounts of PEG4-benzaldehyde-modified IGF-2 peptide (e.g., 1-10× molar excess) to optimize coupling. The variant IGF-2 peptide-conjugated rhGAA (vIGF2-rhGAA) is then purified by size exclusion chromatography or dialysis to remove excess PEG4-azide-modified IGF-2 peptides in acidic pH buffer (50 mM NaOAc, pH 4.8/100 mM NaCl/0.05% Polysorbate-80).

The high-mannose type N-glycans on rhGAA is problematic because it is believed that these carbohydrates cause the protein to be rapidly cleared from the circulation via macrophage and splenic mannose receptors. However, high-mannose type N-glycans can be removed from rhGAA under native (i.e., non-denaturing conditions which preserves catalytic activity) using endoglycosidase F (EndoF) or endoglycosidase H (EndoH) in acidic pH buffer (e.g., 50 mM NaOAc, pH 4.8/100 mM NaCl/0.05% Polysorbate-80) at room temperature. rhGAA has been experimentally shown to remain soluble and is completely active after removal of N-glycans (data not shown). Deglycosylation of rhGAA can be performed after the enzyme is modified with S-Hynic and purified (via size exclusion chromatography or dialysis to remove excess crosslinker). This strategy allows for complete deglycosylation of rhGAA over 1-5 days using EndoF or EndoH without affecting enzyme activity. The deglycosylated hydrazide-modified rhGAA is then conjugated to PEG4-benzaldehyde-modified IGF-2 peptides. Alternatively, rhGAA deglycosylation can be performed concurrently during the conjugation of PEG4-benzaldehyde-modified IGF-2 peptide to hydrazide-modified rhGAA using high concentrations of EndoF or EndoH. Deglycosylated, IGF2 peptide-conjugated rhGAA is then purified by gel filtration chromatography or dialysis to remove excess phosphine-modified IGF-2 peptides and stored in acidic pH buffer (50 mM sodium phosphate, pH 6.2/100 mM NaCl/0.05% Polysorbate-80). The ideal method to remove high-mannose N-glycans from yeast-derived rhGAA would be to co-express EndoH with the lysosomal enzyme for deglycoylation in vivo prior to protein purification of rhGAA. This would generate deglycosylated rhGAA which can be directly modified and coupled to variant targeting peptides without any additional processing.

The above strategies enable the removal of undesirable N-glycans from rhGAA to prevent allergenic responses and to prevent rapid protein clearance while significantly improving binding affinity for the IGF-2/CI-MPR for improved protein targeting and cellular uptake of IGF2 peptide-conjugated lysosomal enzymes. Importantly, this strategy can utilize lysosomal enzymes produced from non-mammalian systems and represent a much more cost-effective approach for developing superior ERTs.

The above examples are designed for increasing the affinity of different lysosomal enzymes for the IGF-2/CI-MPR via chemical conjugation of modified IGF-2 peptides. This strategy improves protein targeting for current and future ERTs to develop superior treatments for LSDs.

Example 6

Figure 6A:
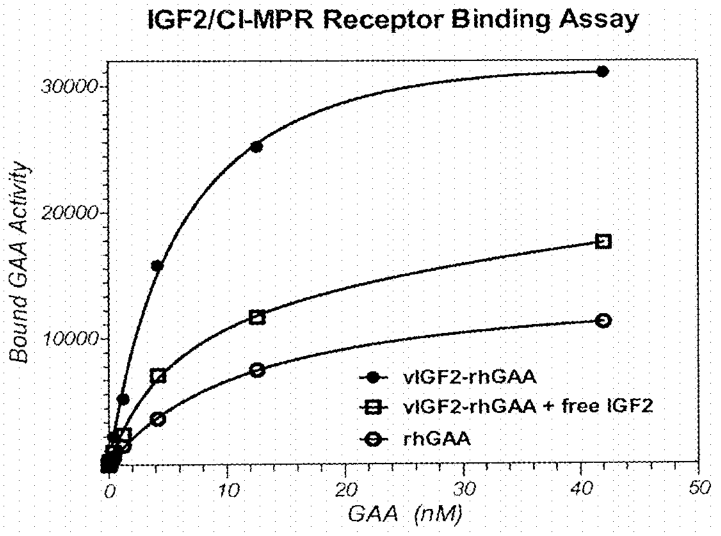
FIGS. 6A and 6B show evaluation of variant IGF2 peptide-conjugated rhGAA for receptor binding and cellular uptake. Variant IGF2 peptide was modified with the crosslinker PEG4-PFB and subsequently coupled to S-Hynic-modified rhGAA. The resultant variant IGF2 peptide-conjugated rhGAA (designated as vIGF2-rhGAA) was then purified by size exclusion chromatography. To determine if chemical conjugation of variant IGF2 peptide improves rhGAA affinity for the IGF2/CI-MPR receptor, the binding of unconjugated rhGAA and vIGF2-rhGAA was directly compared at varying protein concentrations (0.003-10 μg/ml corresponding to 0.012-42 nM rhGAA) in receptor plate binding assays FIG. 6A. Significantly higher amounts of captured enzyme activity were observed for vIGF2-rhGAA than for unconjugated rhGAA at all protein concentrations tested in these IGF2/CI-MPR receptor plate binding assays. These results confirm that conjugation of IGF2 peptide increases rhGAA affinity for the IGF2/CI-MPR receptor. Moreover, the inclusion of free wildtype IGF2 peptide greatly reduced vIGF2-rhGAA capture in these plate assays indicating that binding was dependent on IGF2 peptide. Much higher amounts of free wildtype IGF2 peptide is likely required to completely eliminate vIGF2-rhGAA binding in these receptor plate assays. To determine whether increased receptor affinity would lead to improved cellular uptake for vIGF2-rhGAA, the internalization of extracellular unconjugated rhGAA and vIGF2-rhGAA was evaluated in L6 rat skeletal muscle myoblasts FIG. 6B. vIGF2-rhGAA was shown to be internalized substantially better than unconjugated rhGAA in L6 myoblasts at all protein concentrations tested. These results demonstrate the functional benefit of improving receptor binding affinity for enhancing internalization and delivery of exogenous lysosomal enzymes in target cells.
Figure 7A:
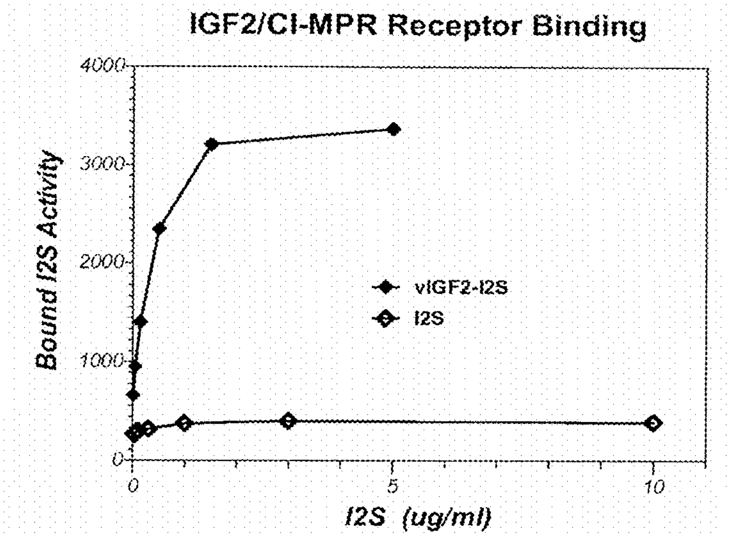
FIGS. 7A and 7B show characterization of variant IGF2 peptide-conjugated I2S. Variant IGF2 peptide was modified with the crosslinker NHS-PEG4-azide and subsequently coupled to phosphine-modified I2S. The resultant variant IGF2 peptide-conjugated I2S (designated as vIGF2-I2S) was purified by size exclusion chromatography. To determine if chemical conjugation of variant IGF2 peptide improves I2S affinity for the IGF2/CI-MPR receptor, the binding of unconjugated I2S and vIGF2-I2S was directly compared at varying protein concentrations (0.03-10 μg/ml) in receptor plate binding assays FIG. 7A. Substantially higher amounts of vIGF2-I2S were captured in these IGF2/CI-MPR receptor plate binding assays than unconjugated I2S at all protein concentrations tested. These receptor binding results are consistent with those for vIGF2-rhGAA and show that the same variant IGF2 peptide can be chemically coupled to different lysosomal enzymes to increase their binding affinity for the IGF2/CI-MPR receptor. To determine whether multiple variant IGF2 peptides can be chemically conjugated to lysosomal enzymes, the molecular mass of unconjugated I2S and vIGF2-I2S was compared by sodium dodecylsulfate polyacrylamide gel electrophoresis (SDS-PAGE) FIG. 7B. Unconjugated I2S had an apparent molecular weight of approximately 80 kDa (lane 1) on SDS-PAGE while vIGF2-I2S had a much higher apparent molecular weight of approximately 120 kDa (lane 2). These data indicate that multiple variant IGF2 peptides must have been chemically conjugated onto I2S for an increase of approximately 40 kDa since the molecular mass for variant IGF2 peptide is only ~8 kDa (lane 3). These results also show that I2S was completely converted to vIGF2-I2S with varying amounts of variant IGF2 peptides as evidenced by the broad protein band on SDS-PAGE.

An IGF2/CI-MPR receptor binding assay was utilized to assess the effects of chemical conjugation of IGF2 peptide on receptor affinity for lysosomal enzymes rhGAA and I2S. This assay is designed to differentiate lysosomal enzymes with high binding affinity for the IGF2/CI-MPR from those with low to moderate binding since unbound lysosomal enzymes are washed away during processing. Moreover, since varying protein concentrations of the lysosomal enzymes are used to assess binding, this assay can determine the protein concentrations required for binding receptor which can be utilized to estimate binding affinity for each lysosomal enzyme preparation. Specifically, unmodified lysosomal enzymes and IGF2 peptide-conjugated lysosomal enzymes were serially diluted in 40 mM HEPES (pH 6.7)/150 mM NaCl/10 mM EDTA and then incubated in 96-well ELISA plates which were coated with IGF2/CI-MPR receptor (50 μl per well of receptor at 6 μg/mlin phosphate buffered saline; then blocked with 2% BSA in phosphate buffered saline) for 1 hr at 30° C. The plates were subsequently washed three times with the same buffer containing 0.1% Tween-20 to remove unbound proteins. The bound lysosomal enzymes were then measured by enzyme activity using the appropriate fluorogenic substrates (e.g., 4-methylumbelliferyl-α-D-glucopyranoside (4-MU-α-Glc) for rhGAA) in assay buffer (50 mM NaOAc, pH 4.8/2% BSA/0.02% Triton X-100) at 37° C. for 1 hr. The samples were then transferred to new 96-well plates, 0.1M NaOH was added to raise the pH of solution to approximately 10.5 and the plates were read in a fluorescence plate reader at the appropriate excitation and emission wavelengths (i.e., 370 nm excitation & 460 nm emission for 4-MU). Our results show that much higher amounts of bound enzyme activity were observed for vIGF2-rhGAA than unconjugated rhGAA at all protein concentrations tested as shown in FIG. 6A. The binding of vIGF2-rhGAA to IGF2/CI-MPR plates was reduced significantly by the inclusion of free WT human IGF2 peptide indicating that this binding was dependent on IGF2 peptide. Much higher amounts of free WT human IGF2 peptide is likely required for complete blockade of vIGF2-rhGAA to IGF2/CI-MPR. Chemical conjugation of IGF2 peptide onto I2 S was also shown substantially increase binding affinity of that enzyme for the IGF2/CI-MPR (FIG. 7A). Moreover, similar amounts of bound I2S activities were observed at 1 and 3 μg/ml for the IGF2 peptide-conjugated I2S (vIGF2-I2S) which indicates that receptor binding was saturated.

These collective data uncovered several important features of the variant IGF2 peptide-conjugation approach. (1) The protein structure of variant IGF2 peptide is appropriate for high affinity binding to IGF2/CI-MPR receptor. This functional assessment is consistent with our C4 reverse phase chromatography data that show wildtype and variant IGF2 peptides bind and elute at nearly identical conditions as shown in FIGS. 5A-5C. Since the "fingerprints" of these two IGF2 peptides are virtually indistinguishable on C4 reverse phase chromatography, they must be very similar in their protein conformations. (2) The chemical conjugation of variant IGF2 peptide did not affect enzyme activity for either rhGAA or I2S (data not shown). The utilization of an extension linker region for chemical coupling of the peptide to lysosomal enzymes likely provided a tether that is sufficient for IGF2 peptide binding while maintaining enzyme activity. (3) The conjugated variant IGF2 peptide is stable and maintains proper protein structure in acidic buffers required for maintaining lysosomal enzyme activities.

The collective data therefore show that chemical conjugation of IGF2 peptide onto lysosomal enzymes (e.g., rhGAA and I2S) can indeed significantly increase their binding affinities for the IGF2/CI-MPR receptor. This approach should theoretically be broadly applicable for chemical conjugation of variant IGF2 peptides onto any lysosomal protein and other non-lysosomal proteins for improving their binding affinity for the IGF2/CI-MPR.

Example 7

Figure 6B:
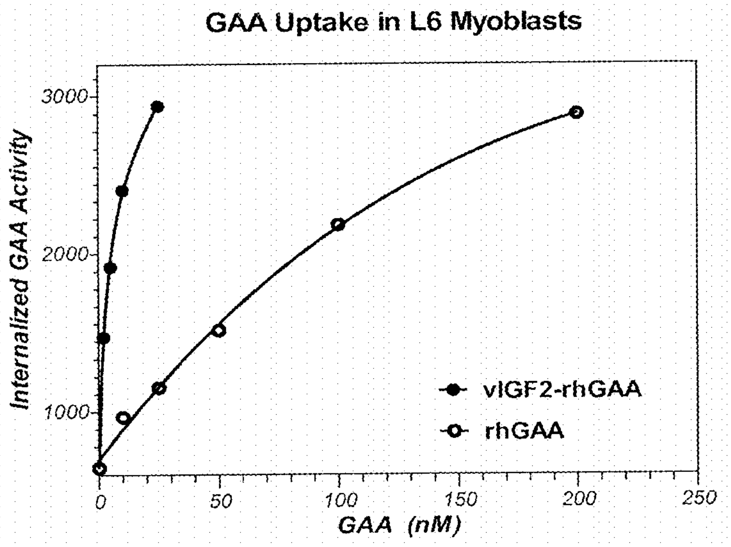

To assess the functional effects of IGF2 peptide for the cellular uptake of exogenous lysosomal enzymes, the internalization of IGF2-conjugated rbGAA (vIGF2-rhGAA) was evaluated in L6 rat skeletal muscle myoblasts. Briefly, L6 myoblasts were expanded in T-75 flasks to confluence in DMEM medium containing 10% fetal bovine serum (FBS) at 37 C and a 5% CO2 environment. The cells were harvested via trypsin/EDTA and plated in 6-well tissue culture plates at a cell density of $3\times10^5$ cells per well and incubated in DMEM/10% PBS medium. Two hours prior to the addition of lysosomal enzymes, the spent DMEM 10% FBS medium was replaced with 2.5 ml uptake medium (Ham's F-12/10% FBS/2 mM PIPES, pH 6.7). Unconjugated rhGAA and vIGF2-rhGAA were diluted to 0.5 mg/ml with 50 mM sodium phosphate, pH 6.5/100 mM NaCl/0.05%>Polysorbate-80 and sterilized through a 0.2 μm filter spin device (Costar). Unconjugated rhGAA was added to individual wells at final protein concentrations of 10-200 nM while vIGF2-rhGAA was added at 2-25 nM. To ensure that all wells had the same volume and correct protein concentration, 50 mM sodium phosphate, pH 6.5/100 mM NaCl/0.05% Polysorbate-80 buffer was added so that the total volume of enzyme and buffer was 0.2 ml for each sample. As shown in FIG. 6B, the internalization of vIGF2-rhGAA was significantly better than unconjugated rhGAA at all protein concentrations tested. These results revealed several important aspects about vIGF2-rhGAA: (1) the protein structure of variant IGF2 peptide is sufficient for high affinity binding to cell surface IGF2/CI-MPR receptors; (2) vIGF2-rhGAA was efficiently internalized in L6 myoblasts and delivered to lysosomes since intracellular organelles were isolated with this protocol; (3) variant IGF2 peptide has low binding affinity to serum IGF binding proteins (IGFBPs) as predicted since vIGF2-rhGAA was internalized in L6 myoblasts rather than being bound to IGBPs in medium; (4) chemical coupling of variant IGF2 peptides did not alter rhGAA enzyme activity.

These results clearly show that chemical coupling of variant IGF2 peptides onto rhGAA can significantly improve its binding affinity for the IGF2/CI-MPR which directly translates into substantially improved cellular uptake of the lysosomal enzyme in target cells. These data suggest that vIGF2-rhGAA would be a superior ERT for the treatment of Pompe disease.

Example 8

Figure 7B:
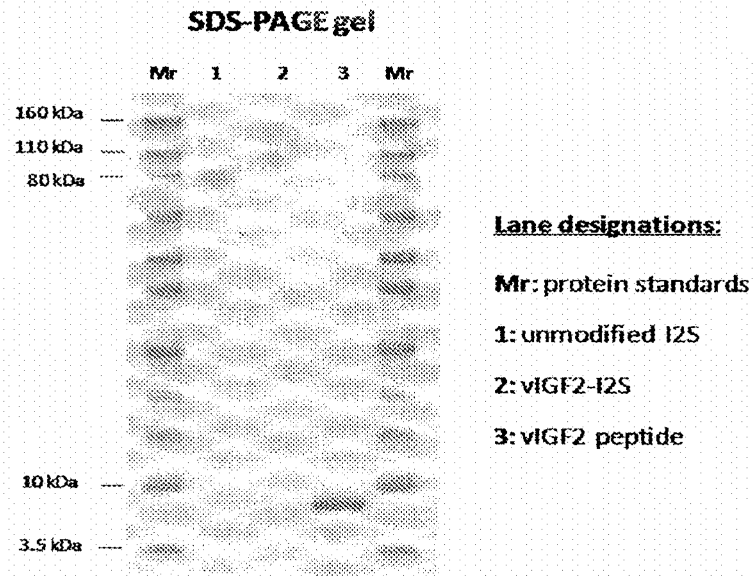

To determine whether multiple IGF2 peptides were chemically conjugated to lysosomal enzymes, sodium dodecylsulfate polyacrylamide protein gel electrophoresis (SDS-PAGE) was utilized to separate proteins based on their size and the gel was subsequently stained with a modified Coomassie blue stain for visualization of protein bands. As shown in FIG. 7B, the molecular weight of recombinant wildtype human iduronidate 2-sulfatase (I2S) was significantly increased from ~80 kDa to approximately 120 kDa after chemical conjugation of variant IGF2 peptide. These data clearly show that multiple variant IGF2 peptides must have been coupled to I2S since the molecular weight of variant IGF2 peptide is approximately only 8 kDa. The stained SDS-PAGE gel shows that there is a distribution of vIGF2-I2S species with varying amounts of attached variant IGF2 peptide with an average of 5 attached peptides per molecule of I2S (corresponding to an increase of ~40 kDa to attain the approximate 120 kDa molecular weight on gel).

Importantly, these data also highlight the potential of this approach for coupling multiple, different peptides onto the same lysosomal enzyme. For example, variant IGF2 peptides and other targeting peptides (e.g., peptides that are known to be transported across the blood brain barrier (BBB)) could be chemically coupled to the same lysosomal enzyme for targeting the lysosomal enzyme to visceral tissues (via IGF2 peptide) and to the brain and central nervous system (via BBB-penetrating peptides). This approach therefore has the potential to overcome the major limitations of current ERTs.

Example 9

SEQ ID NO: 1 represents the cDNA sequence for 8×His-tagged [(del 1-4)-Arg6-Leu27-Arg65] IGF-2 peptide with an N-terminal extension linker region and a TEV protease recognition site (optimized for expression in *E. coli*).

SEQ ID NO: 1

```
atgggcagccaccaccaccatcatcaccaccacactagtgccggcgagaa
tctgtactttcagggcggtggtggtagcggcggtggtggtagccgtaccc
tgtgtggtggcgaattggttgatacgctgcaattcgtctgtggtgaccgc
ggtttcctgttctctcgtccggcgtcccgcgtgagccgtcgcagccgtgg
tatcgttgaagagtgctgttttcgtagctgcgacctggctctgctggaaa
cctattgcgcgaccccggcacgtagcgagtga
```

SEQ ID NO: 2: represents the amino acid sequence for variant IGF2 peptide with the extension sequence.

SEQ ID NO: 2

```
NH2-GGGGSGGGGSRTLCGGELVDTLQPVCGDRGFLFSRPASRVSRRSRG
IVEECCFRSCDLA LLETYCATPARSE-COOH
```

SEQ ID NO: 2 corresponds to a variant IGF2 peptide after removal of N-terminal 8× His tag via TEV protease. This variant IGF2 peptide lacks residues 1-4 such that the N-terminal serine residue corresponds to residue 5 of WT IGF2. Arginine substituted for glutamic acid at position 6 is known to substantially lower binding affinity of IGF2 peptide for serum IGF binding proteins (IGFBPs). Substitution of leucine for tyrosine at position 27 is known to substantially lower binding affinity of IGF2 peptide for insulin and IGF1 receptors. A conservative substitution of arginine for lysine at position 65 was utilized to enable chemical modification of only the extension linker region at the N-terminus for conjugation to lysosomal enzymes. The N-terminal extension region is represented by SEQ ID NO: 3.

SEQ ID NO: 3

GGGGSGGG

The N-terminal glycine residue in SEQ ID NO:3 is used for chemical modification for coupling to lysosomal enzymes.

Example 10

SEQ ID No: 5 represents the cDNA sequence for 8×His-[(del 1-4)-Arg6-Leu27-Arg65] IGF-2 peptide that was optimized for expression in *E. coli.*

SEQ ID NO:5:

SEQ ID NO: 6:

Nco I

```
CCATGGGCTCAAGCCACCACCACCACCACCACCACCACAGCGGCGAGAACCTGTACTTTCAGAGCCGTACCTTGTGC
GGTGGTGAGCTGGTGGATACTCTGCAATTTGTTTGCGGCGACCGCGGCTTCCTGTTCAGCCGTCCGGCGAGCCGTGT
TTCCCGTCGTAGCCGTGGTATCGTCGAAGAGTGTTGTTTCCGCTCTTGTGACCTGGCGCTGCTGGAAACGTATTGCG
CTACCCCGGCACGCTCGGAAGGTGGTGGCGGCAGCGGTGGTGGTAGCAAAGGTTGAGCGGCCGCATAAGCGGCCGCA
TAAT
```

Not I

ORF for Optimized 8XHis-Modified IGF-2 Peptide:

```
3    atgggctcaagccaccaccaccaccaccaccaccacagcggcgag
      M  G  S  S  H  H  H  H  H  H  H  H  S  G  E
48   aacctgtactttcagagccgtaccttgtgcggtggtgagctggtg
      N  L  Y  F  Q  S  R  T  L  C  G  G  E  L  V
93   gatactctgcaatttgtttgcggcgaccgcggcttcctgttcagc
      D  T  L  Q  F  V  C  G  D  R  G  F  L  F  S
138  cgtccggcgagccgtgtttcccgtcgtagccgtggtatcgtcgaa
      R  P  A  S  R  V  S  R  R  S  R  G  I  V  E
183  gagtgttgtttccgctcttgtgacctggcgctgctggaaacgtat
      E  C  C  F  R  S  C  D  L  A  L  L  E  T  Y
228  tgcgctaccccggcacgctcggaaggtggtggcggcagcggtggt
      C  A  T  P  A  R  S  E  G  G  G  G  S  G  G
273  ggtagcaaaggttga 287
      G  S  K  G  *
```

SEQ ID NO: 6 represents the amino acid sequence for a variant IGF2 peptide with the extension sequence.

```
SEQ ID NO: 6:
NH2-
SRTLCGGELVDTLQFVCGDRGFLFSRPASRVSRRSRGIVEECCFRSCDLAL

LETYCATPARSEGGGGSGGGSKG-COOH
```

SEQ ID NO: 6 corresponds to a variant IGF2 peptide after removal of N-terminal 8×His tag via TEV protease. The TEV protease recognition site is underlined above. This variant JGF2 peptide lacks residues 1-4 such that the N-terminal serine residue corresponds to residue 5 of WT IGF2. Arginine substituted for glutamic acid at position 6 is known to substantially lower binding affinity of IGF2 peptide for serum IGF binding proteins (IGFBPs). Substitution of leucine for tyrosine at position 27 is known to substantially lower binding affinity of JGF2 peptide for insulin and JGF1 receptors. A conservative substitution of arginine for lysine at position 65 was utilized to incorporate a lysine residue within extension region to enable chemical modification and conjugation to lysosomal enzymes. The extension region is represented by SEQ ID NO: 7.

```
SEQ ID NO: 7:
GGGGSGGGSKG
```

The lysine residue in SEQ ID NO:7 is used for chemical modification for coupling to lysosomal enzymes.

What is claimed:

1. A conjugate, comprising:

a variant IGF-2 peptide chemically conjugated to a recombinant human lysosomal the variant IGF-2 peptide comprises SEQ ID NO:2 or SEQ ID NO:6 or, comprises one or more of the following modifications with respect to SEQ ID NO: 8:

substitution of arginine for glutamic acid at position 6;

deletion of amino acids 1-4 and 6;

deletion of amino acids 1-4, 6 and 7;

deletion of amino acids 1-4 and 6 and substitution of lysine for threonine at position 7;

deletion of amino acids 1-4 and substitution of glycine for glutamic acid at position 6 and substitution of lysine for threonine at position 7;

substitution of leucine for tyrosine at position 27;

substitution of leucine for valine at position 43;

substitution of arginine for lysine at position 65; and the IGF-2 peptide further comprises an affinity tag and/or a linker extension region.

2. The conjugate of claim 1, wherein the recombinant human lysosomal enzyme comprises one or more modified lysine residues, a chemically modified N-terminus, or a combination thereof.

3. The conjugate of claim 1, wherein the recombinant human lysosomal enzyme is human acid a-glucosidase (rhGAA).

4. The conjugate of claim 1, wherein the chemical conjugation is via a cross linking agent comprises an aminoreactive bifunctional cross linker.

5. The conjugate of claim 1, wherein the chemical conjugation is via a cross linking agent comprises N-succinimidyl 6-hydrazinonicotinate acetone (S-Hynic).

6. The conjugate of claim 1, wherein the chemical conjugation is via a cross linking agent comprises sulfo-Nhydroxysuccinimide ester-phosphine (sulfo-NHS-phosphine).

7. The conjugate of claim 1, wherein the-chemical conjugation is via a cross linking agent comprises N-hydroxysuccinimide ester-tetraoxapentadecane acetylene (NHS-PEG4-acetylene).

8. The conjugate of claim 1, wherein the chemical conjugation is via a crosslinking agent comprises heterobifunctional cross linkers selected from difluorocyclooctyne (DIFO) and dibenzocyclooctyne (DIBO).

9. A method for treating a subject suffering from a lysosomal storage disease, the method comprising administering to the subject the conjugate of claim 1 in an amount sufficient to treat the lysosomal storage disease.

10. The method of claim 9, wherein the lysosomal storage disease is at least one of the following: Pompe Disease, Fabry Disease, and Gaucher Disease, MPS I, MPS II, MPS VII, Tay Sachs, Sandhoff, a-mannosidosis, and Wohlman disease.

11. The method of claim 10, wherein the lysosomal storage disease is Pompe Disease.

12. The method of claim 10, wherein the lysosomal storage disease is Fabry Disease.

13. The method of claim 10, wherein the lysosomal storage disease is Gaucher Disease.

14. The conjugate of claim 1, wherein the IGF-2 peptide comprises SEQ ID NO:2.

15. The conjugate of claim 1, wherein the IGF-2 peptide comprises SEQ ID NO:6.

16. The conjugate of claim 1, wherein the IGF-2 peptide further comprises a linker, wherein said linker is 5 to 20 amino acid residues in length.

17. The conjugate of claim 16, wherein said linker is about 10 amino acid residues in length.

18. The conjugate of claim 16, wherein said linker comprises SEQ ID NO:3.

19. The conjugate of claim 16, wherein said linker comprises SEQ ID NO:7.

* * * * *

SEQUENCE LISTING

```
<160> NUMBER OF SEQ ID NOS: 8

<210> SEQ ID NO 1
<211> LENGTH: 282
<212> TYPE: DNA
<213> ORGANISM: Artificial Sequence
<220> FEATURE:
<223> OTHER INFORMATION: Synthetic polynucleotide

<400> SEQUENCE: 1

atgggcagcc accaccacca tcatcaccac cacactagtg ccggcgagaa tctgtacttt      60

cagggcggtg gtggtagcgg cggtggtggt agccgtaccc tgtgtggtgg cgaattggtt     120

gatacgctgc aattcgtctg tggtgaccgc ggtttcctgt tctctcgtcc ggcgtcccgc     180

gtgagccgtc gcagccgtgg tatcgttgaa gagtgctgtt ttcgtagctg cgacctggct     240

ctgctggaaa cctattgcgc gaccccggca cgtagcgagt ga                        282


<210> SEQ ID NO 2
<211> LENGTH: 72
<212> TYPE: PRT
<213> ORGANISM: Artificial Sequence
<220> FEATURE:
<223> OTHER INFORMATION: Synthetic polypeptide

<400> SEQUENCE: 2

Gly Gly Gly Gly Ser Gly Gly Gly Gly Ser Arg Thr Leu Cys Gly Gly
1               5                   10                  15

Glu Leu Val Asp Thr Leu Gln Phe Val Cys Gly Asp Arg Gly Phe Leu
            20                  25                  30

Phe Ser Arg Pro Ala Ser Arg Val Ser Arg Arg Ser Arg Gly Ile Val
        35                  40                  45

Glu Glu Cys Cys Phe Arg Ser Cys Asp Leu Ala Leu Leu Glu Thr Tyr
    50                  55                  60

Cys Ala Thr Pro Ala Arg Ser Glu
65                  70


<210> SEQ ID NO 3
<211> LENGTH: 8
<212> TYPE: PRT
<213> ORGANISM: Artificial Sequence
<220> FEATURE:
<223> OTHER INFORMATION: Synthetic peptide

<400> SEQUENCE: 3

Gly Gly Gly Gly Ser Gly Gly Gly
1               5
```

-continued

<210> SEQ ID NO 4
<211> LENGTH: 8
<212> TYPE: PRT
<213> ORGANISM: Artificial Sequence
<220> FEATURE:
<223> OTHER INFORMATION: Synthetic 8xHis tag

<400> SEQUENCE: 4

His His His His His His His His
1               5

<210> SEQ ID NO 5
<211> LENGTH: 285
<212> TYPE: DNA
<213> ORGANISM: Artificial Sequence
<220> FEATURE:
<223> OTHER INFORMATION: Artificial polynucleotide

<400> SEQUENCE: 5
atgggctcaa gccaccacca ccaccaccac caccacagcg gcgagaacct gtactttcag     60
agccgtacct tgtgcggtgg tgagctggtg gatactctgc aatttgtttg cggcgaccgc    120
ggcttcctgt tcagccgtcc ggcgagccgt gtttcccgtc gtagccgtgg tatcgtcgaa    180
gagtgttgtt tccgctcttg tgacctggcg ctgctggaaa cgtattgcgc taccccggca    240
cgctcggaag gtggtggcgg cagcggtggt ggtagcaaag gttga                    285

<210> SEQ ID NO 6
<211> LENGTH: 74
<212> TYPE: PRT
<213> ORGANISM: Artificial Sequence
<220> FEATURE:
<223> OTHER INFORMATION: Artificial polypeptide

<400> SEQUENCE: 6

Ser Arg Thr Leu Cys Gly Gly Glu Leu Val Asp Thr Leu Gln Phe Val
1               5                   10                  15

Cys Gly Asp Arg Gly Phe Leu Phe Ser Arg Pro Ala Ser Arg Val Ser
            20                  25                  30

Arg Arg Ser Arg Gly Ile Val Glu Glu Cys Cys Phe Arg Ser Cys Asp
        35                  40                  45

Leu Ala Leu Leu Glu Thr Tyr Cys Ala Thr Pro Ala Arg Ser Glu Gly
    50                  55                  60

Gly Gly Gly Ser Gly Gly Gly Ser Lys Gly
65                  70

<210> SEQ ID NO 7
<211> LENGTH: 11
<212> TYPE: PRT
<213> ORGANISM: Artificial Sequence
<220> FEATURE:
<223> OTHER INFORMATION: Artificial peptide

<400> SEQUENCE: 7

Gly Gly Gly Gly Ser Gly Gly Gly Ser Lys Gly
1               5                   10

<210> SEQ ID NO 8
<211> LENGTH: 67
<212> TYPE: PRT
<213> ORGANISM: Homo sapiens

-continued

```
<400> SEQUENCE: 8

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
            20                  25                  30

Ser Arg Val Ser Arg Arg Ser Arg Gly Ile Val Glu Glu Cys Cys Phe
        35                  40                  45

Arg Ser Cys Asp Leu Ala Leu Leu Glu Thr Tyr Cys Ala Thr Pro Ala
    50                  55                  60

Lys Ser Glu
65
```